United States Patent [19]
Kuhn et al.

[11] Patent Number: 5,516,864
[45] Date of Patent: May 14, 1996

[54] FLUORESCENT ION-SELECTIVE DIARYLDIAZA CROWN ETHER CONJUGATES

[75] Inventors: Michael A. Kuhn; Richard P. Haugland, both of Eugene, Oreg.

[73] Assignee: Molecular Probes, Inc., Eugene, Oreg.

[21] Appl. No.: 375,360

[22] Filed: Jan. 19, 1995

Related U.S. Application Data

[62] Division of Ser. No. 38,918, Mar. 29, 1993, Pat. No. 5,405,975.
[51] Int. Cl.⁶ ............ C07D 321/00; C07D 273/08; G01N 31/22; C08F 26/08
[52] U.S. Cl. ............ 526/263; 526/238.1; 526/238.2; 526/238.3; 527/200; 527/312; 528/403; 528/423; 530/300; 530/350; 536/17.3; 536/55; 536/55.1; 540/467; 549/223; 549/224; 549/227
[58] Field of Search ............ 540/467; 549/223, 549/224, 227; 526/238.1, 238.2, 238.3, 263; 527/200, 312; 528/403, 423; 530/300, 350; 536/17.3, 55.1, 55

[56] References Cited

U.S. PATENT DOCUMENTS

| | | | |
|---|---|---|---|
| 4,603,209 | 10/1986 | Tsien et al. | 548/236 |
| 5,049,673 | 11/1991 | Tsien et al. | 546/107 |
| 5,133,934 | 5/1992 | Denton et al. | 422/56 |
| 5,134,232 | 4/1992 | Tsien et al. | 540/467 |
| 5,154,890 | 9/1992 | Mauze et al. | 422/82.07 |
| 5,227,487 | 8/1993 | Haugland et al. | 546/15 |

FOREIGN PATENT DOCUMENTS

0284691A1  4/1988  European Pat. Off. .

OTHER PUBLICATIONS

Haugland, Handbook of Fluorescent Probes and Research Chemicals (1992).
Fery-Forgues, et al., New J. Chem., 14, 617 (1990).
Bradshaw, et al., J. Org. Chem., 53, 3190 (1988).
Hayashita, et al., Anal. Chem., 63, 1844 (1991).
Yoshikami, et al., Biophys. J. 64, A221 (1993).

*Primary Examiner*—Richard L. Schilling
*Attorney, Agent, or Firm*—Allegra J. Helfenstein; Anton E. Skaugset

[57] ABSTRACT

This invention describes novel sensors for ions that are based on the combination of xanthylium-based dyes with metal-binding N,N'-diaryldiaza crown ethers. These sensors are primarily useful for detection and quantitation of alkali-metal ions in aqueous solution. Binding of the ion results in a change in the fluorescence properties of the indicating dye that can be correlated with the ion concentration. Methods are provided for attaching reactive groups on these sensors for conjugation to dyes, lipids and polymers and for enhancing entry of the indicators into living cells.

30 Claims, 8 Drawing Sheets

FLUORESCENT ION-SELECTIVE DIARYLDIAZA CROWN ETHER CONJUGATES

This application is a division of application Ser. No. 08/038,918 filed Mar. 29, 1993, now U.S. Pat. No. 5,405,975.

FIELD OF THE INVENTION

This invention relates to fluorescent indicators for alkali-metal ions in aqueous solution. In particular, the indicators are derived from xanthylium fluorophores combined with N,N'-diaryldiaza crown ethers that bind with the ions, resulting in a spectral change of the indicator. The indicators contain a reactive group that can be used for attaching another fluorophore, a polymer, or a lipid.

BACKGROUND

Optical indicators for ions are important for qualitative and quantitative determination of ions, particularly in living cells. Fluorescent indicators for alkali metal ions, in particular $Na^+$ and $K^+$, permit the continuous or intermittent optical determination of these ions in living cells. Such indicators are also useful for measuring ions in extracellular spaces; in vesicles; in vascular tissue of plants and animals; biological fluids such as blood and urine; in fermentation media; in environmental samples such as water, soil, waste water and seawater; and in chemical reactors.

Fluorescent indicators are already known for a variety of ions, particularly for biologically important ions such as calcium, magnesium, sodium and potassium. See e.g. Haugland, HANDBOOK OF FLUORESCENT PROBES AND RESEARCH CHEMICALS, Part IV, Set 22 (5th ed. 1992). For most biological applications, it is essential that the indicators be effective in aqueous solutions. It is also important that indicators for biological applications be insensitive to pH changes over the physiological range (pH 6–8) and sensitive to ion concentrations in the physiological range (for sodium, a $K_d$ of about 5 mM to about 20 mM). It is also beneficial if the indicator absorbs and emits light in the visible spectrum where biological materials have low intrinsic absorbance or fluorescence.

Benzofuranyl indicators for alkali metal ions such as $Na^+$, $K^+$, and $Li^+$ are described by Tsien, et al. in U.S. Pat. No. 5,134,232 (1992) for intracellular use. In particular, Tsien, et al. describe fluorescent indicator compounds containing an aza crown ether attached to one or two fluorophores. The preferred compounds of Tsien, et al. (e.g. SBFI, SBFO, SBFP) contain two benzofuranyl fluorophores that contain an additional carboxy-substituted aromatic substituent on the fluorophore.

Although the benzofuranyl indicators described as preferred by Tsien, et al. have improved sensitivity to $Na^+$ and $K^+$ over previously known materials, including other materials claimed in the patent, the preferred indicators are not without disadvantages. The benzofuranyl indicators, particularly SBFO, tend to leak from cells, limiting their effectiveness in intracellular applications. The benzofuranyl indicators are also limited because they are only excitable in the UV (below about 380 nm) rather than in the visible range. Use of a UV excitation wavelength usually results in more background signal from contaminants in the sample and a greater likelihood of phototoxicity to living cells. In addition, when an indicator is incorporated in a fiber optic sensor, the transmittance of light in a fiber optic is significantly greater at visible wavelengths than in the ultraviolet. Furthermore, benzofuranyl indicators with shorter wavelength excitation cannot be used optimally with instruments such as flow cytometers and confocal microscopes that use the argon laser for excitation (at 488 nm).

A fluorescent N-phenyl-monoaza crown ether containing a benzoxazinone fluorophore (BOZ-crown) or a merocyanine laser dye (DCM-crown) is described by Fery-Forgues, et al., NEW J. CHEM 14, 617 (1990). The fluorescent monoaza crown ethers have absorption maxima in acetonitrile of 490 nm and 464 nm respectively. Like the materials of Tsien, et al., the fluorophore is linked to the crown phenyl substituent by a trans-ethylenic linkage, except that it is rotatable instead of fixed. Unlike the materials described by Tsien, et al., however, these compounds cannot be used in aqueous environments because even minute amounts of water appear to cause a shift to non-linearity in the fluorescence response to ion binding. Furthermore, this type of fluorophore typically has a low fluorescence yield in water and the compounds described have low water solubility.

None of the crown ether compounds described above are conjugated to other materials that assist in localizing or retaining the indicators inside the cell, or used for preparing conjugates with polymers. There is a need for fluorescent indicators for alkali-metal ions that can be attached to polymers for use in remote sensing of ions or enhancing the solubility or localization of the optical sensor. The advantage of conjugation of the indicator to water-soluble polymers to improve retention of other ion indicators in the cytosol has been described in Haugland, HANDBOOK OF FLUORESCENT PROBES AND RESEARCH CHEMICALS, supra, but Haugland does not describe indicators for alkali-metal ions conjugated to polymers or other materials.

U.S. Pat. No. 5,133,934 describes a hydrophobic career incorporating a bis crown ether compound and a reporter substance. Although the patent mentions that fluorescent indicators can be used as reporter substances, the preferred reporter substance (the only one evaluated) is a nonfluorescent compound 7-decyl-MEDPIN. Other nonfluorescent crown ethers on a solid support have been described. The use of (allyloxy)methyl-substituted diaza crown ethers that have been covalently bonded to silica gel for separation of certain heavy metal ions, is described by Bradshaw, et al., J. ORG. CHEM. 53, 3190 (1988). Selective column concentration of alkali-metal ions using crown ethers is described by Hyashita, et al., ANAL. CHEM. 63, 1844 (1991).

There is a need for fluorescent ion indicators with desirable spectral properties, that also can be covalently coupled to polymers, lipids, or other solid phase materials or intracellular or extracellular components. There is need further for indicators that can function in aqueous solution and whose spectral properties facilitate detection in the visible range. The novel indicator compounds containing xanthylium fluorophores described herein differ from previously described materials in that they have improved spectral properties and sensitivity that enhance their use as indicators of trace amounts of biologically important ions of alkali-metals. The xanthylium indicators have a high absorbance in the visible spectrum (generally with an extinction coefficient of at least 60,000 $cm^{-1}M^{-1}$ for indicators containing one xanthylium dye to greater than about 120,000 $cm^{-1}M^{-1}$ for those containing two xanthylium dyes) and bright long wavelength fluorescence of the metal-indicator complex (generally a quantum yield of greater than about 0.2). Furthermore, they are useful in aqueous solutions and can be covalently reacted with a variety of materials. The covalent attachment as well as desirable spectral properties also make the materials useful in remote sensing devices, particularly where attachment to a solid phase is required.

SUMMARY OF THE INVENTION INCLUDING DESCRIPTION OF SPECIFIC EMBODIMENTS

Figure 1:
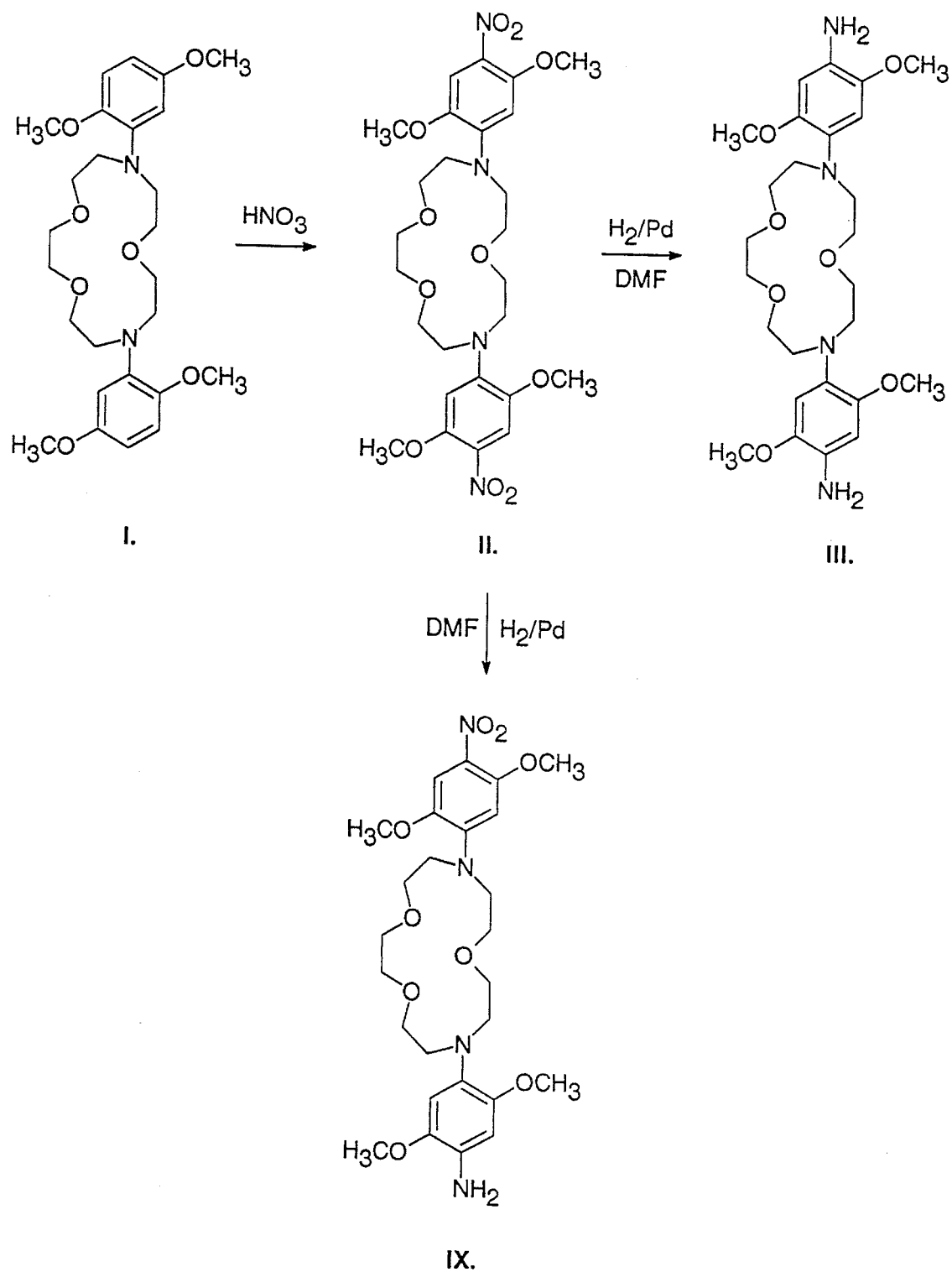
FIG. 1: Synthetic pathway to di and mono amine substituted diaryl crown ethers (Compounds III and IX).
Figure 2:
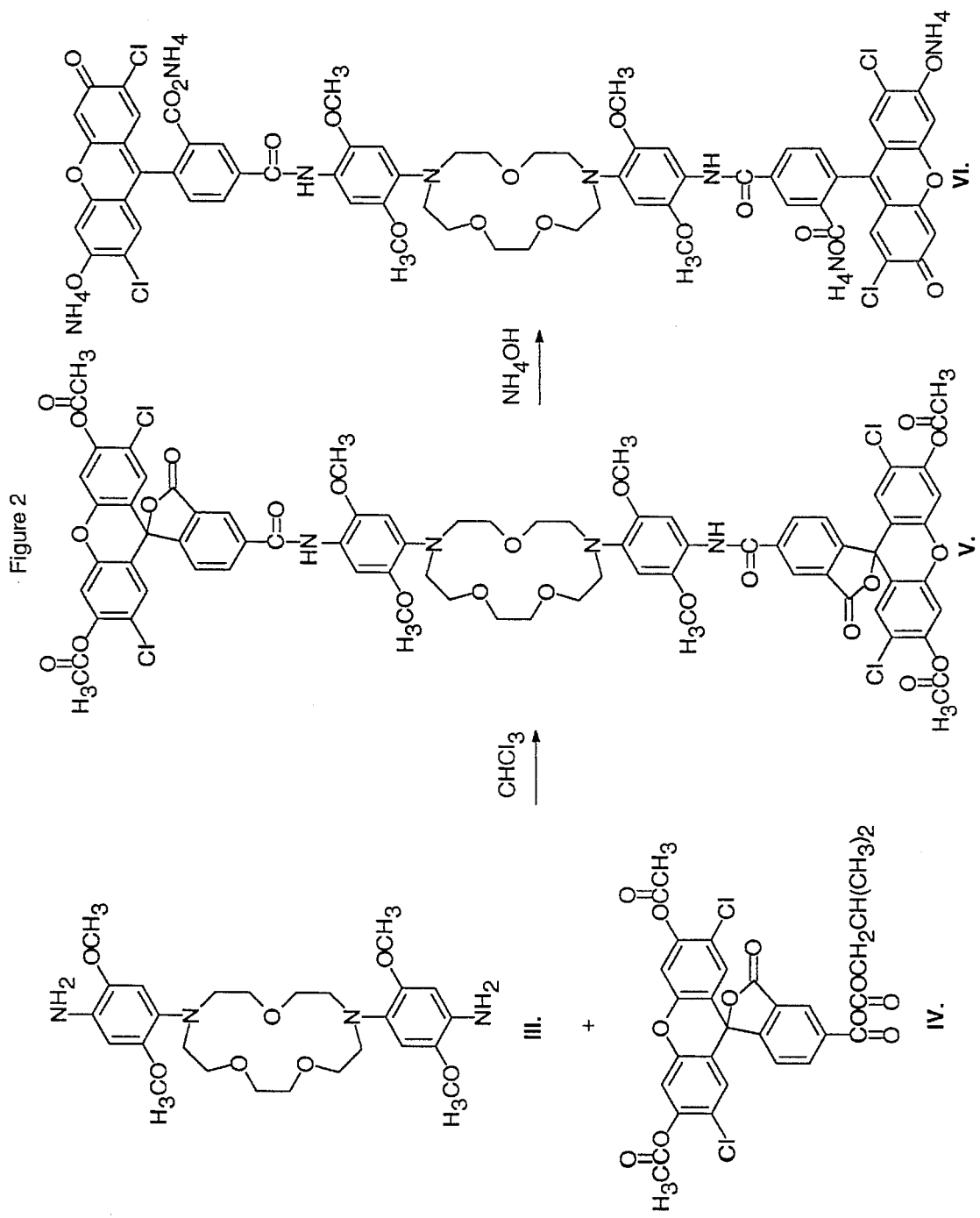
FIG. 2: Synthetic pathway to a bis-(4-amino-2,5-dimethoxyphenyl)-diazatrioxa crown ether conjugated to two identical green fluorescent dyes (2',7'-dichlorofluorescein) by carboxamide linkages (Compound VI).
Figure 3:
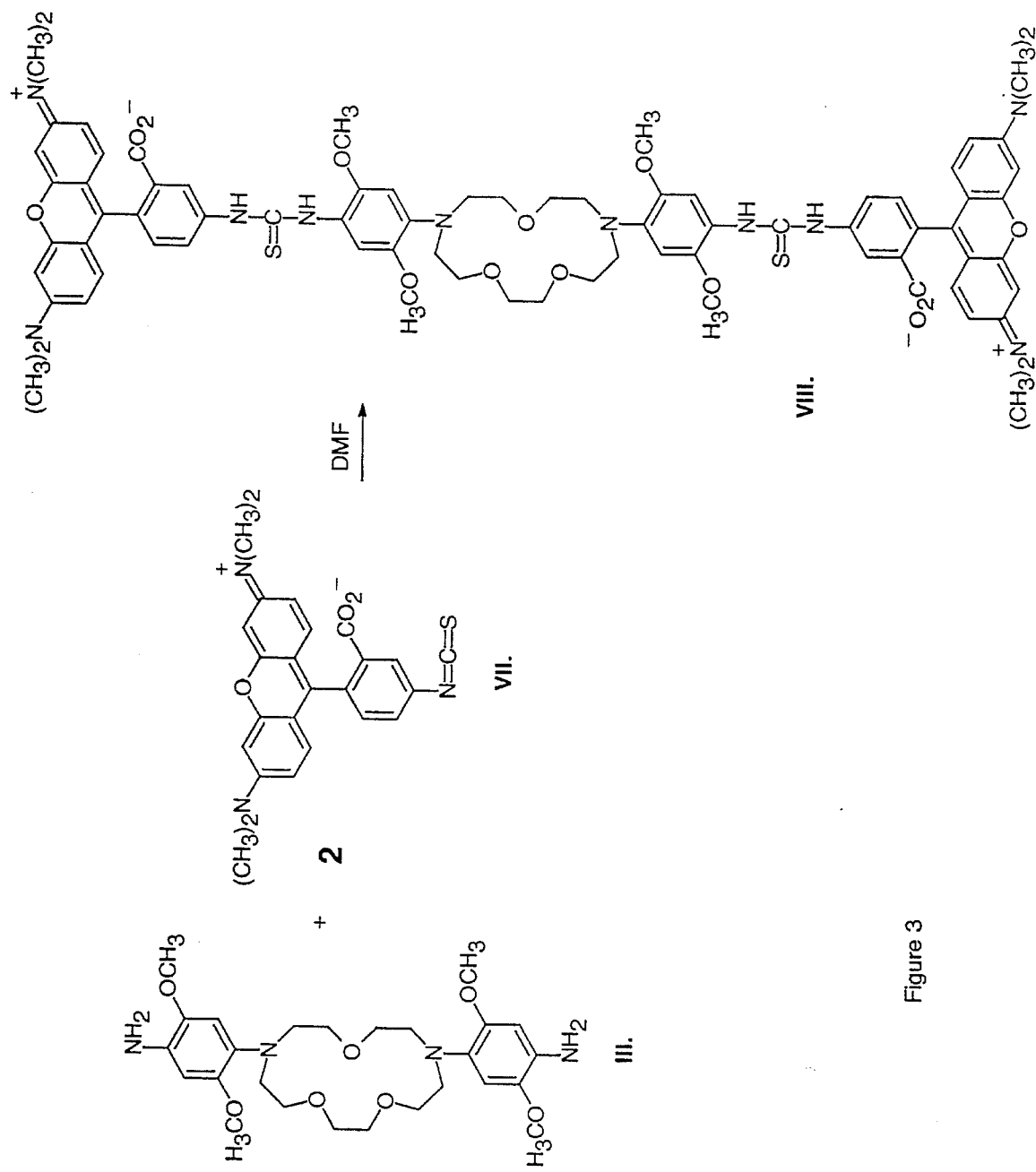
FIG. 3: Synthetic pathway to a diaryldiazatrioxa crown ether conjugated to two identical orange fluorescent dyes (tetramethylrhodamine-5-isothiocyanate) by thiourea linkages (Compound VIII).
Figure 4:
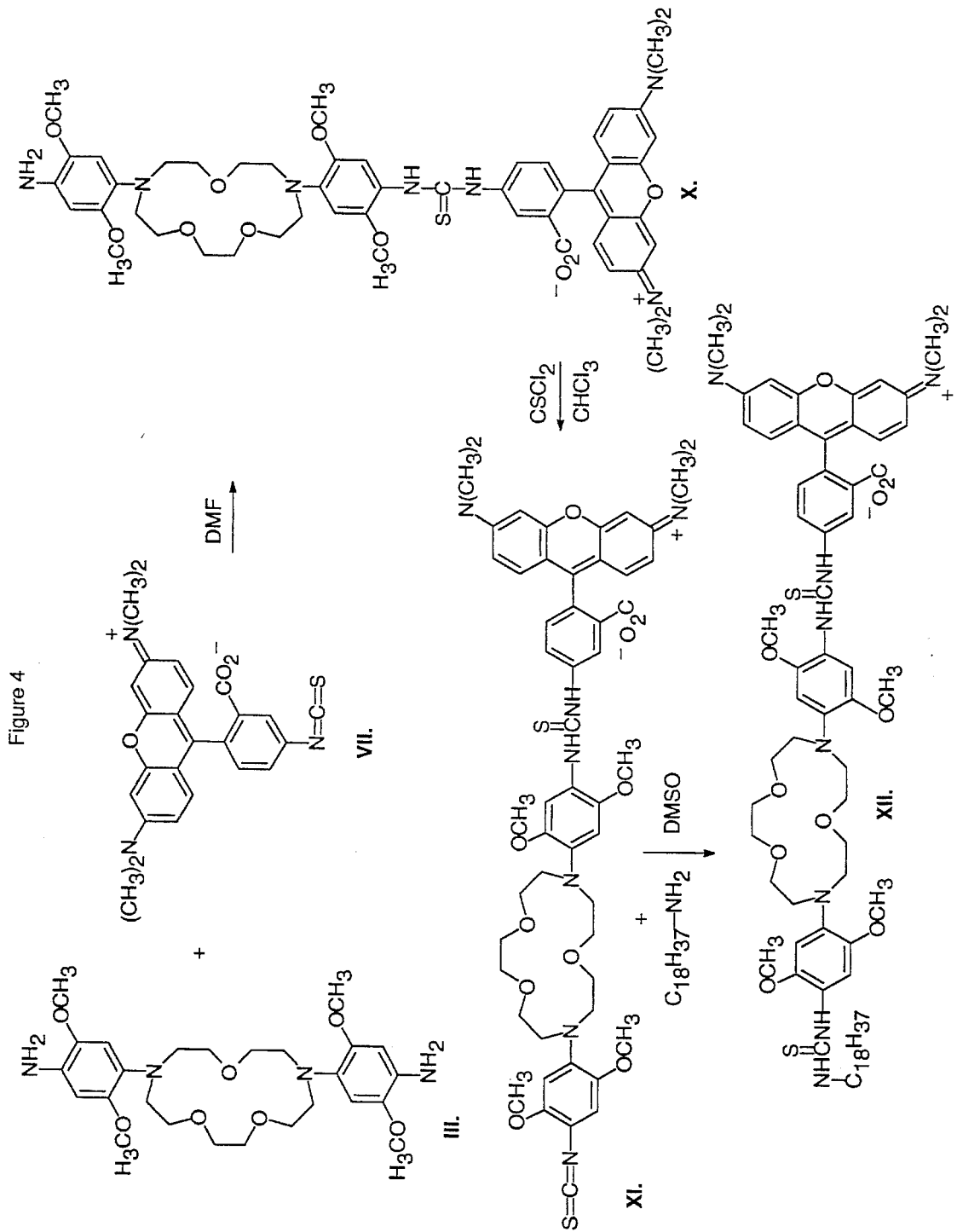
FIG. 4: Synthetic pathway to a conjugate of diaryldiazatrioxa crown ether with one orange fluorescent dye (tetramethylrhodamine) linked by a thiourea linkage and one single chain lipid (Compound XII).
Figure 5:
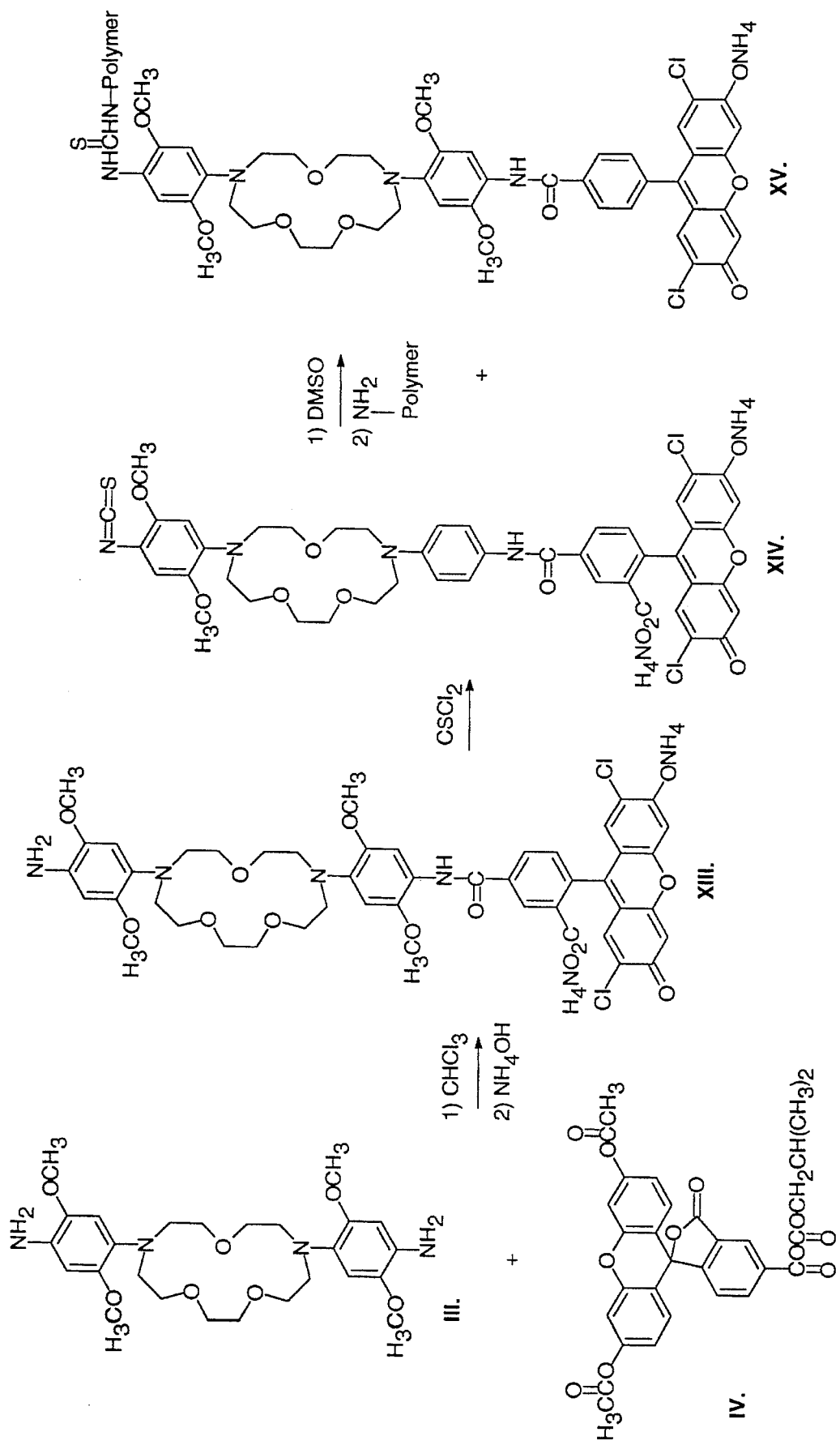
FIG. 5: Synthetic pathway to a conjugate of diaryldiazatfioxa crown ether with one green fluorescent dye (2', 7'-dichlorofluorescein) and one water soluble polymer (Compound XV).

The indicators of this invention have the general structure:

A-CROWN-B where A is a first substituted aryl group that contains a first xanthylium-based fluorophore and B is a second substituted aryl group that contains a second xanthylium-based fluorophore, a reactive group, a lipid or a polymer. CROWN is a diaza crown ether. The crown ether varies in size, containing from 4–6 "points" in the crown. Each "point" is —$CH_2CH_2$—Y—, where Y is N or O, such that two of the Y atoms in the crown are N (crown nitrogens). The crown ether may be symmetrical or asymmetrical, i.e. the number of points on either side of the crown nitrogens are the same or different, respectively. The carbon atoms of the crown ethers of this invention are preferably substituted only by hydrogen atoms.

CROWN is a site that provides the residues required for ion binding. In the subject derivatives, CROWN is an N,N'-diaryldiaza crown ether with the general structure:

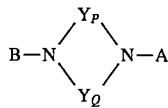

wherein $Y_p$ is —($CH_2CH_2$—O)$_j$—$CH_2CH_2$— and $Y_Q$ is —($CH_2CH_2$—O)$_k$—$CH_2CH_2$—; j and k are independently 1 or 2; A and B are substituted aryl groups as defined below.

The crown ethers of this invention are described herein according to the nomenclature: diaza(number of ring atoms)crown-number of noncarbon ring atoms; i.e. from smallest to largest: diaza(12)crown-4 or in shorthand (DA12C4), diaza(15)crown-5 (DA15C5), diaza(18)crown-6 (DA18C6). By modification of the number of ethylidene groups in CROWN, the affinity and selectivity for binding a given ion can be modified. Typically when $Na^+$ is the ion to be detected, CROWN is DA15C5; when $K^+$ is the ion to be detected, CROWN is DA18C6; when $Li^+$ is the ion to be detected, CROWN is DA12C4.

The substituted aryl group A has the formula:

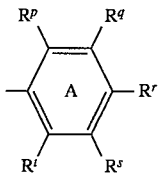

wherein one of $R^p$, $R^q$, $R^r$, $R^s$ or $R^t$ is a first fluorophore FLUOR that is bonded to the aryl group A at $R^p$, $R^q$, $R^r$, $R^s$ or $R^t$ according to the formula:

—($R^a$)$_n$($R^b$)$_{n'}$-FLUOR where —($R^a$)$_n$($R^b$)$_{n'}$— defines the covalent linkage between FLUOR and the aryl group A at $R^p$, $R^q$, $R^r$, $R^s$ or $R^t$. The subscripts n and n' are independently 0 or 1. Where n and n' are 0, the linkage is a covalent bond. When n=1, $R^a$ is —$OCH_2R^3$—, —$OR^{3'}$—, —$SR^3$—, —$SR^{3'}$—, —NH(C=O)$CH_2R^3$—, —NH(C=O)$R^{3'}$—, —(=O)NHCH$_2R^3$—, —(C=O)NH$R^{3'}$—, —NHSO$_2R^3$—, —NHSO$_2R^{3'}$—, —NH(C=O)NHCH$_2R^3$—, —NH(C=O)NH$R^{3'}$—, —NH(C=S)NHCH$_2R^3$—, or —NH(C=S)NH$R^{3'}$—, where $R^3$ is (CH$_2$)$_m$ and m+1–6, and $R^{3'}$ is phenylene (—$C_6H_4$—), carboxyphenylene (—$C_6H_3$COOH—) or sulfophenylene (—$C_6H_3SO_3H$—) or their pharmaceutically acceptable salts or esters. When n'=1, $R^b$ is —NH—, —NH(C=O)—, —NH(C=S)—, —S—, —O—, —(C=O)—; or —CH$_2$— or —(C=O)CH$_2$—. Preferred —$R^aR^b$— are single bonds, ethers, carboxamides, ureas, thioureas and sulfonamides. Also preferred, particularly where -FLUOR is an aryl-substituted xanthylium dye, $R^a$ is —NH(C=O)$R^{3'}$—, —NHSO$_2R^{3'}$—, or —NH(C=S)NH$R^{3'}$—, where $R^{3'}$ carboxyphenylene (—$C_6H_3$COOH—) or sulfophenylene (—$C_6H_3SO_3H$—) and their pharmaceutically acceptable salts and esters. Preferably, FLUOR is attached at $R^r$, para to the crown ether attachment site.

The fluorophore -FLUOR is a substituted xanthylium dye that absorbs maximally at greater than about 490 nm. As used herein, a substituted xanthylium dye is a fluorescent compound that contains at least three fused 6-membered rings, where the center ring contains an oxygen heteroatom; a xanthylium dye optionally has the aryl substituent typically found in these fluorophores (e.g. in fluorescein, rhodamine, etc.) or it is optionally absent. The xanthylium dye, including the aryl-substituted xanthylium dye, is typically substituted by one or more amino or hydroxy substituents and is optionally fused to one or more benzene rings that may, in turn be substituted by one or more amino or hydroxy substituents. Amino substituents may be substituted by lower alkyl substituents with <5 carbons or incorporated in saturated heterocyclic rings that are fused to the xanthylium dye such as in rhodamine 101. Additional permitted substituents on FLUOR, which may be the same or different, include hydrogen, halogen, carboxy, sulfo, alkyl, perfluoroalkyl, alkoxy and carboxyalkyl (each with <7 carbons). Examples of xanthylium derivatives include, but are not limited to pyronines, xanthenes, fluoresceins, rhodamines, rosamines, rhodols, benzofluoresceins, dibenzofluoresceins, seminaphthofluoresceins and naphthofluoresceins and their substituted derivatives. Additionally, FLUOR is optionally a pharmaceutically acceptable ester or salt of the xanthylium dye. Preferred esters are acetate and acetoxymethyl. Preferred salts are lithium, sodium, potassium or ammonium or mono- or polyalkylammonium.

Chemically reactive, commercially available xanthylium fluorophores that are useful in synthesizing the compounds of this invention are described in Haugland, HANDBOOK OF FLUORESCENT PROBES AND RESEARCH CHEMICALS (5th ed. 1992) (incorporated herein by reference) and include, among others, fluorescein- 5-isothiocyanate; tetramethylrhodamine-6-isothiocyanate; 5-carboxyfluorescein; 5-carboxytetramethylrhodamine; 5-carboxy rhodol derivatives (and other rhodol derivatives described in U.S. Ser. No. 07/509,360 (filed Apr. 16, 1990) incorporated by reference); rhodamine 101 sulfonyl chloride (TEXAS RED™); 5-carboxy-2',7'-dichlorofluorescein; 5-carboxyseminaphthofluorescein; 5-carboxynaphthofluorescein; 5-(dichlorotriazinyl)aminofluorescein; eosin-5-iodoacetamide; 5-bromomethylfluorescein; fluorescein-5-maleimide; 5-aminofluorescein; and Lissamine rhodamine B sulfonyl cadaverine.

The remainder of the substituents $R^p$, $R^q$, $R^r$, $R^s$ and $R^t$ that do not contain a fluorophore (remaining A substituents) are independently H, $CH_3$, $NO_2$, $CF_3$, F, Cl, Br, I, —$OR^5$, —(C=O)$OR^5$, or —$OCH_2$(C=O)$OR^5$, where $R^5$ is an alkyl group with about 1–6 carbons, a benzyl ($C_6H_5CH_2$—, an alpha-acyloxyalkyl, a pharmaceutically acceptable esterifying group, or a pharmaceutically acceptable salt.

As used throughout this document, pharmaceutically acceptable salt means non-toxic salts of carboxylic acids known and used in the pharmaceutical industry, such as $K^+$, $Na^+$, $Cs^+$, $Li^+$, $Ca^{2+}$, $Mg^{2+}$, $NR_4^+$ where R=H or $C_1$–$C_4$ alkyl, or combinations thereof, or combinations of acid salts of these counterions plus free acid groups. Pharmaceutically acceptable esterifying groups are those that form readily hydrolyzable esters which are known and used in the pharmaceutical industry, such as alpha-acyloxyalkyl esters, especially acetoxymethyl ($CH_3CO_2CH_2$—) esters.

The incorporation of the non-functional-group remaining A substituents listed above can be used to enhance the affinity of the ion-selective molecule for polycations (such as the lower alkyl groups, methyl and ethyl) or lessen the affinity (such as carboxylic acid derivatives, nitro, cyano, trifluoromethyl and halogens such as chlorine, bromine and iodine). These substituents can also be added after the reactive version of the indicator is attached to other materials as described below.

The other crown nitrogen of the indicator is attached to aryl group B that has the formula:

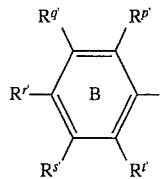

where at least one of $R^{p'}$, $R^{q'}$, $R^{r'}$, $R^{s'}$ or $R^{t'}$ is $(R^{a'})_n(R^{b'})_{n'}$—X. X is a reactive terminus $R^x$ or the product of reaction of $R^x$ with a second substituted xanthylium dye (-FLUOR'), with a polymolecular assembly (-POLY), or with a lipophilic moiety (-LIPID). As used throughout this document, a reactive terminus is a terminal group that can readily chemically react with a reactive site on another natural or synthetic molecule to allow the aryl-substituted crown ether to be covalently coupled to the other molecule. The group —$(R^{a'})_n(R^{b'})_{n'}$— defines the covalent linkage between X and the aryl group B at $R^{p'}$, $R^{q'}$, $R^{r'}$, $R^{s'}$ or $R^{t'}$. The subscripts n and n' are independently 0 or 1. Where n' are 0, the linkage is a covalent bond. When n=1, $R^{a'}$ is —$OCH_2R^3$—, —$OR^3$—, —$SR^3$—, —$SR^{3'}$—, —NH(C=O)$CH_2R^3$—, —NH(C=O)$R^{3'}$—, —(C=O)NH$CH_2R^3$—, —(C=O)NH$R^{3'}$—, —NHSO$_2R^3$—, —NHSO$_2R^{3'}$—, —NH(C=O)NH$CH_2R^3$—, —NH(C=O)NH$R^{3'}$—, —NH(C=S)NH$CH_2R^3$—, or —NH(C=S)NH$R^{3'}$—, where $R^3$ is $(CH_2)_m$ and m=1–6, and $R^{3'}$ is phenylene (—$C_6H_4$—), carboxyphenylene (—$C_6H_3$COOH—) or sulfophenylene (—$C_6H_3SO_3H$—) or their pharmaceutically acceptable salts or esters. When n'=1, $R^{b'}$ is —NH—, —NH(C=O)—, —NH(C=S)—, —S—, —O—, —(C=O)—; or —$CH_2$— or —(C=O)$CH_2$—. Preferred —$R^{a'}R^{b'}$— are single bonds, ethers, carboxamides, ureas, thioureas and sulfonamides. Also preferred, particularly where X is an aryl-substituted xanthylium dye, $R^{a'}$ is —NH(C=O)$R^{3'}$—, —NHSO$_2R^{3'}$—, or —NH(C=S)NH$R^{3'}$—, where $R^{3'}$ is carboxyphenylene (—$C_6H_3$COOH—) or sulfophenylene (—$C_6H_3SO_3H$—) and their pharmaceutically acceptable salts and esters.

The most common reactive terminus is a carboxylic acid or a derivative thereof including a succinimidyl ester, acyl azide, anhydride, or acid halide. Other groups that can be used for the reactive terminus include amines, isocyanates, isothiocyanates, haloacetamides, acrylamides, alcohols, phenols, aldehydes, imido esters, sulfonate esters, alkyl and aryl halides, sulfonyl halides, hydrazines and maleimides. Preferably, the reactive terminus is an amine or aniline, an isocyanate or isothiocyanate, a haloacetamide, an alkyl halide, a carboxylic acid, an anhydride or an activated ester. Table 1 lists some common reactive terminus groups and the reactive sites with which they most commonly react spontaneously at room temperature under near neutral pH. The table does not include all possible reactive groups since with the appropriate choice of solvent, temperature and catalysts, other groups can be made to react.

TABLE 1

| REACTIVE GROUPS | | |
|---|---|---|
| REACTIVE TERMINUS ($R^x$) | REACT WITH: (on other molecules) | TO YIELD: (linkage) |
| alcohols/phenols | alkyl halides | ethers |
| alcohols/phenols | acids | esters |
| alcohols/phenols | isocyanates | urethanes |

TABLE 1-continued

REACTIVE GROUPS

| REACTIVE TERMINUS ($R^x$) | REACT WITH: (on other molecules) | TO YIELD: (linkage) |
|---|---|---|
| alcohols/phenols | silyl halides | silicates |
| haloacetamides | thiols | thioethers |
| maleimides | thiols | thioethers |
| alkyl halides | thiols | thioethers |
| alkyl sulfonates | thiols | thioethers |
| alkyl halides | alcohols/phenols | ethers |
| alkyl sulfonates | alcohols/phenols | ethers |
| isocyanates | alcohols/phenols | urethanes |
| thiols | haloacetamides | thioethers |
| thiols | maleimides | thioethers |
| amines/anilines | sulfonyl halides | sulfonamides |
| amines/anilines | carboxylic acids | carboxamides |
| amines/anilines | anhydrides | carboxamides |
| amines/anilines | activated esters* | carboxamides |
| alkyl halides | amines | alkyl amines |
| activated esters* | amines | carboxamides |
| carboxylic acids | amines/anilines | carboxamides |
| anhydrides | amines/anilines | carboxamides |
| acyl halides | amines/anilines | carboxamides |
| aryl azides | amines/anilines | carboxamides/ureas |
| isocyanates | amines/anilines | ureas |
| isothiocyanates | amines/anilines | thioureas |
| acrylamides | alkylenes | polyalkylenes |

*activated esters, as understood in the art, generally have the formula —COΩ, where Ω is a good leaving group (e.g. oxysuccinimidyl (—$OC_4H_4O_2$),-1-oxybenzotriazolyl ($C_6H_4N_3O$—); or a phenoxy group or phenoxy substituted one or more times by electron withdrawing substituents such as nitro, fluoro, chloro, cyano, or trifluoromethyl, or combinations thereof, used to form activated phenyl esters; or a carboxylic acid activated by a carbodiimide to form an anhydride or mixed anhydride —$OCOR^8$ or —$OCNR^8NHR^9$, where $R^8$ and $R^9$, which may be the same or different, are $C_1$–$C_6$ alkyl, $C_1$–$C_6$ perfluoroalkyl, or $C_1$–$C_6$ alkoxy; or cyclohexyl, 3-dimethylaminopropyl, or N-morpholinoethyl).

The reactive terminus $R^x$ chemically reacts with the reactive site on another natural or synthetic molecule to form a conjugate:

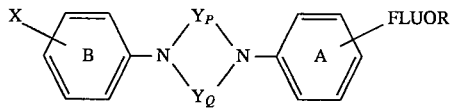

In one embodiment of the invention X is a second substituted xanthylium fluorophore (-FLUOR') that may be the same as or different from FLUOR. Preferably FLUOR is identical to FLUOR'. When X is FLUOR'—$(R^{a'})_n(R^{b'})_{n'}$— is preferably a single bond, an ether, a carboxamide, a urea, a thiourea, a sulfonamide, and, particularly where X is an aryl-substituted xanthylium dye, $R^{a'}$ is —NH(C=O)$R^{3'}$—, —NHSO$_2R^{3'}$—, or —NH(C=S)NH$R^{3'}$—, where $R^{3'}$ is carboxyphenylene ($_{C_6}H_3$COOH—) or sulfophenylene (—$C_6H_3SO_3H$—) and their pharmaceutically acceptable salts and esters.

In another embodiment of the invention X is a lipophilic moiety LIPID that is covalently attached at the B side of CROWN. As used throughout this document, a lipophilic moiety confers water-repelling properties on a molecule or a part of a molecule. Typical lipophilic moieties are lipid chains that are straight or branched aliphatic chains that contain greater than about six carbon atoms such as alkyl groups, fatty acid derivatives, phospholipids, glycerides, polyethylene or similar lipophilic materials. LIPID may also contain cyclic structures as part of a lipid chain, such as in cholesterol or other sterol derivatives. Oxygen and sulfur heteroatoms may also be present in the lipid chain as in polyoxyethylene. Lipid chains containing greater than about 30 catenated nonhydrogen atoms are of limited use. Preferably, LIPID contains between about 12 and 24 linear carbon atoms, more preferably 16–18 linear carbons. LIPID derivatives of the indicators are useful in synthesizing labeled liposomes described below. When X is LIPID, the preferred linkage —$(R^{a'})_n(R^{b'})_{n'}$— is a single bond, an ether or an amide.

In yet another modification of the invention, X is a polymolecular assembly (-POLY) that is bound covalently to the B side of CROWN. A wide variety of natural and synthetic materials are suitable for use in this embodiment of the invention. As used herein, polymolecular assembly means a high molecular weight material made up of repeating or nonrepeating units of relatively smaller molecules linked together to form a discrete compound. The repeating units may be linked covalently, as in polymers such as polystyrene or polysaccharides, or may be linked noncovalently as in liposomes and micelles, or may be linked by a combination of covalent bonds and noncovalent attractions, as in polypeptides, proteins, oligonucleotides and nucleic acids, with significant degrees of secondary and tertiary structure.

POLY has an average molecular weight of greater than about 750 Daltons, preferably from about 2000 to about 10,000,000 Daltons, more preferably from about 10,000 to about 500,000 Daltons. The molecular weight of such materials is almost always polydisperse. Preferably POLY is a biocompatible material. As used herein, biologically-compatible materials are suitable for or customarily used in biological systems, usually because of a low generalized intrinsic interaction with biological materials, i.e. the biologically compatible materials are generally inert toward biological materials (e.g. glass) or have a specific intrinsic interaction with biological materials (e.g. antibodies or nucleic acids). Suitable polymolecular assemblies may be soluble in water or organic solvents or may be insoluble or may be rendered insoluble, such as by having cross-linking groups.

Suitable polymeric assembly substituents include but are not limited to synthetic polymeric resins and gels such as polystyrene and polyacrylic acids, amides, and esters; glass; polyols such as polyvinyl alcohol and polysaccharides such as agarose, cellulose, dextrans, ficols, heparin, glycogen, amylopectin, mannan, inulin, and starch; polypeptides and proteins; and oligonucleotides and nucleic acids; and also include naturally and chemically crosslinked forms thereof. Preferred water soluble POLY are dextrans, water soluble proteins (especially antibodies), nucleic acids (particularly DNA, RNA and synthetic oligonucleotides), and polyacrylic acids, amides and esters. Preferred water insoluble POLY are water-insoluble polymeric materials such as agarose and polystyrene, latex microparticles, glass, and natural and synthetic liposomes.

Preferably the polymolecular assembly POLY possesses one or more reactive sites such as amines, alcohols (including phenols) and thiols, that readily react with the reactive terminus group $R^x$ on the indicator. $R^x$ groups such as acrylamides can be copolymerized with monomers to form covalently-modified polymers. Natural or synthetic polymolecular assemblies that do not inherently possess reactive sites that readily react with the reactive terminus on the indicator (see Table 1), may be modified, by methods well known and documented in the art, to add reactive sites to the polymolecular assembly with which the reactive terminus groups of the indicator will readily form covalent bonds. Numerous suitable polymolecular assemblies that are polymers or modified polymers, especially dextrans and proteins, that are useful in the synthesis of compounds of this invention are commercially available from suppliers such as Bio-Rad, Polysciences and Pharmacia. These polymers can be further modified using heterobifunctional crosslinking reagents (HBCL from Molecular Probes, Inc., Eugene, Oreg.) to introduce an even wider variety of reactive sites on polymers for use in this invention.

Commonly the indicator is modified by attachment of a polymolecular assembly that is water miscible or immiscible. POLY derivatives of the indicators can be used to localize the indicator such as by attachment to an antibody that binds to a class of cells or to a specific intra- or extra-cellular location. POLY can also be used to bind the indicator essentially irreversibly to a spot such as the tip of a fiber optic. Furthermore, attachment of the indicator to POLY can be used to improve the aqueous solubility, reduce the membrane permeability and reduce the likelihood of nonspecific binding of the indicator to cellular components or bodily fluids. Lipophilic polymers can be incorporated to reduce the solubility of the indicator in an aqueous medium, or to immobilize the indicator in a plastic matrix, liposomes or similar environments. Examples of suitable POLY include polysaccharides such as dextrans, peptides and proteins, liposomes and polystyrene. The materials of this invention in which X is POLY continue to be effective in detecting dilute ion concentrations while attached to such polymers, whether immobilized on a solid phase by such polymer attachment or remaining in solution. Alternatively other suitable embodiments of the indicator may be bound noncovalently to a polymer such as by hydrophobic or ionic interactions or trapped in a gel-sol matrix or dissolved in latex.

The remainder of the substituents $R^p$, $R^q$, $R^r$, $R^s$ or $R^t$ that are not $(R^{a'})_n(R^{b'})_n$—X (remaining B substituents) are independently H, $CH_3$, $NO_2$, $CF_3$, F, Cl, Br, I, —$OR^5$, —(C=O)$OR^5$, or —$OCH_2$(C=O)$OR^5$, where $R^5$ is an alkyl group with about 1–6 carbons, a benzyl ($C_6H_5CH_2$—), an alpha-acyloxyalkyl or a pharmaceutically acceptable esterifying or a pharmaceutically acceptable salt. As with remaining A substituents, incorporation of the non-functional-group remaining B substituents can be used to enhance or lessen the affinity of the ion-selective molecule for polycations. These substituents can also be added after the reactive version of the indicator is attached to other materials as described above.

Diaryldiaza Crown Ether Synthesis and Modification

The key intermediates for synthesis of the fluorescent indicator conjugates are N,N'-diaryldiaza crown ethers containing appropriate substituents for attachment or formation of the linking groups, reactive groups and X. Several methods exist for synthesis of these intermediates: 1. modification of known N,N'-diaryl crown ethers; 2. modification of known diaza crown ethers in which both nitrogen atoms are substituted by hydrogen; 3. complete synthesis of the crown ether from appropriately-substituted anilines.

Several useful diaza crown ethers that contain 4–8 ethylidene (—$CH_2CH_2$—) groups are commercially available. Synthesis of N,N'-diphenyldiaza crown ethers has been described in U.S. Pat. 5,134,232 to Tsien, et al. (1992) (incorporated by reference), These can be modified to provide the required chemical reactivity. For instance N,N'-bis-(p-nitrophenyl)DA18C6 can be synthesized from N,N'-diphenylDA18C6 by nitration and the product hydrogenated over Pd catalyst to N,N'-bis-(p-aminophenyl)DA18C6. Molecules such as this are useful precursors to ion-selective fluorescent indicator conjugates that contain two fluorophores (Examples 4, 17, 18) or that contain one fluorophore and a reactive group (Examples 6, 7, 9, 10, and 13) or one fluorophore with a polymolecular assembly (Examples 11, 12, and 14) or a lipid (Example 8). By changing the number of ethylidene groups to greater or fewer, fluorescent indicators that have selectivity for larger or smaller ions, respectively can be obtained.

A more generally useful synthesis of the required disubstituted-aryl derivatives involves reaction of a diaza crown ether with a first-arylating group that is $R^pR^qR^rR^sR^t$phenyl-Z where $R^pR^qR^rR^sR^t$phenyl- is a penta-substituted phenyl that contains substituents to which the fluorophore can be covalently attached or that can be converted by subsequent chemical reaction to these reactive groups and Z is a chemical functional group that can be replaced by the nitrogen atom of the diaza crown ether by a chemical reaction. Commonly the substituents $R^p$, $R^q$, $R^r$, $R^s$ or $R^t$ that are, or can be, made reactive are nitro, cyano, formyl, amino, hydroxy, mercapto, carboxy (or derivatives of amino, hydroxy, mercapto or carboxy). Other substituents $R^p$, $R^q$, $R^r$, $R^s$ or $R^t$ that may be incorporated either to provide desirable spectral, ion binding, cell permeability, polarity, chemical reactivity or other properties include, but are not limited to: hydrogen, alkoxy, alkyl, haloalkyl or esters with about 1–6 carbons, $CF_3$, cyano, sulfo, F, Cl, Br, I, and benzyl ($C_6H_5CH_2$—). Examples of Z include the halogens F, Cl, Br and I (particularly F and I), but may also include other groups such as —$SO_3$—Na. Electron withdrawing groups such as nitro, trifluoromethyl and cyano typically facilitate reaction of $R^pR^qR^rR^sR^t$phenyl-Z with the diaza crown ether. Commonly the diaza crown ether is reacted with an excess of $R^pR^qR^rR^sR^t$phenyl-Z to produce an N,N'-bis-($R^pR^qR^rR^sR^t$phenyl)-diaza crown ether. Less commonly a relatively stoichiometric molar quantity of $R^pR^qR^rR^sR^t$phenyl-Z is reacted with the diaza crown ether to produce an N-($R^pR^qR^rR^sR^t$phenyl)diaza crown ether containing a residual NH functionality and this intermediate is reacted with a second-arylating group that is $R^pR^qR^rR^sR^t$phenyl-Z to yield an unsymmetrically-substituted N-($R^pR^qR^rR^sR^t$phenyl)-N'-($R^pR^qR^rR^sR^t$phenyl) diaza crown ether (Example 15). This product is subsequently modified by selective chemical reactions to yield the subject fluorescent ion-indicating conjugates.

Other methods exist for preparing aryl-substituted diaza crown ethers. Among these is the synthesis of symmetric N,N'-bis-(2,5-dimethoxyphenyl)diaza crown ethers prepared by reaction of a diaza crown ether with quinone to yield an intermediate N,N'-bis-(2,5-dihydroxyphenyl)diaza crown ether, which can be alkylated to a N,N'-bis-(2,5-dimethoxyphenyl) crown ether (Compound 1, U.S. Pat. No. 5,134,232 to Tsien, et al., 1992).

The third general means of synthesizing appropriately-substituted crown ethers consists of reaction of an excess of an aniline derivative $R^pR^qR^rR^sR^t$phenyl-$NH_2$ with a reagent L—$CH_2CH_2$—(O$CH_2CH_2$)$_n$—L where n=1–4 and L is a group such as Cl, Br, I or a sulfonate ester that is readily replaced by reaction with an aniline to yield an alkylated aniline intermediate $R^pR^qR^rR^sR^t$phenyl-NH-($CH_2CH_2O)_nCH_2CH_2$—NH-phenyl $R^pR^qR^rR^sR^t$. This intermediate can be cyclized to a crown ether either by reaction with a second mole of L—$CH_2CH_2$—(O$CH_2CH_2$)$_n$—L or by a two step sequence that, for instance, involves reaction of an acid chloride of the corresponding acid HOOC$CH_2$—(O$CH_2CH_2$)$_{n-1}$—O$CH_2$COOH to yield an amide that is chemically reduced by a reducing agent such as lithium aluminum hydride to the N,N-bis-($R^pR^qR^rR^sR^t$phenyl)diaza crown ether. Although asymmetrically-substituted diaza crown ethers can be synthesized by this method, it is usually preferred to synthesize them by one of the other methods that have been described.

The ion-sensing fluorophore is usually incorporated into the indicator by subsequent chemical modifications of the aryl residues of the crown ether, although it is also possible to synthesize these by alternative means such as formation of the crown ether from some amino-substituted fluorophores by an alkylation or acylation sequence as described for the general synthesis of crown ethers above. For instance fluorescent ion indicators containing xanthylium fluorophores can be conveniently prepared by reaction of an aromatic or aliphatic amine on the crown ether with an amine-reactive group such as an acid chloride, anhydride, isocyanate, isothiocyanate on the xanthylium fluorophore. Alternatively, the reactive groups on the xanthylium fluorophore and the crown ether can be reversed. Other combinations include, but are not limited to, reaction of alcohols, thiols, phenols or thiophenols with alkylating agents such as alkyl halides or alkyl sulfonates or with acylating agents such as acid chlorides, anhydrides or isocyanates.

When the reactive group is not already present on the crown ether or fluorescent dye, other groups can be activated by means well known to one skilled in the art including:

1) reaction of carboxylic acids with thionyl chloride; with N-hydroxysuccinimide and a carbodiimide; or with a chloroformate and triethylamine (Example 3; compound IV) to give acid chlorides, succinimidyl esters or anhydrides respectively;
2) reaction of a sulfonic acid with thionyl chloride and dimethylformamide to give a sulfonyl chloride;
3) reaction of an amine with phosgene or thiophosgene (Examples 7 and 10) to yield an isocyanate or an isothiocyanate;
4) reaction of an amine with acryloyl chloride to yield an acrylamide;
5) rearrangement of an acyl azide to an isocyanate on heating; or
6) reaction of an amine with iodoacetic anhydride to give an iodoacetamide (Example 13) or with maleic anhydride followed by acetic anhydride/sodium acetate to yield a maleimide.

A wide variety of chemically-reactive or potentially chemically-reactive and fluorescent fluorescein, rhodamine, rhodol, benzoxanthenes, dibenzoxanthene and other xanthene oxygen heterocycles that absorb maximally beyond about 490 nm are commercially available as described by Haugland, HANDBOOK OF FLUORESCENT PROBES AND RESEARCH CHEMICALS (5th ed. 1992), as described above, or in other literature references. The nature of the bond that links the xanthylium fluorophore to the crown ether appears to have limited effect on the optical response of the fluorophore to ion binding. Acceptability of the linking chemistry can be determined by titration of the resultant indicator with the ion of interest over the target range of response (Examples 19–22). Commonly the xanthylium fluorophore is bonded to the crown ether through a linkage that is a carboxamide, sulfonamide, urea, thiourea, urethane, ether or thioether or without intervening atoms. Less commonly the linkage is through an alkyl or aryl linking group or an ester. Fluorophores can be directly coupled to the aryl group of the crown ether without any linking atoms by various reactions. For instance, the brominated diaryldiaza crown ether can be coupled to a xanthone derivative through the intermediacy of a lithium salt in a reaction similar to one described in U.S. Pat. No. 5,049,673 to Tsien, et al. (1991) (incorporated by reference) for synthesis of the calcium indicator, fluo-3.

The fluorophore or other functional groups on the indicator may be further modified subsequent to attachment to the crown ether. These modifications may be incorporated either to provide desirable spectral, ion binding, cell permeability, polarity, chemical reactivity or other properties. For applications in measuring the ion content in living cells it is useful to prepare forms of the indicator that have enhanced membrane permeability. These commonly consist of esters of esterifiable groups such as alcohols, phenols or acids that can be removed by action of an intracellular enzyme. Most commonly these are acetoxymethyl esters of carboxylic acids as described in U.S. Pat. No. 4,603,209 to Tsien, et al (1986) (incorporated by reference) or acetate esters of phenols (for instance see Example 3), although other pharmaceutically acceptable derivatives that can be cleaved intracellularly are also possible. For instance t-butyldimethylsilyl esters of indicators that contain carboxylic acids have been shown to spontaneously hydrolyze intracellularly to the carboxylic acid by Yoshikami et al., BIOPHYS. J. 64, A221 (1993).

Other modifications may be incorporated to prevent the indicator from passing through a membrane or to improve retention of the indicator in cells or compartments of cells. Examples of this are incorporation of sulfonic acids, water-soluble polymers (Example 11) or incorporation of reactive groups such as chloro- or bromomethyl that will react with intracellular thiol-containing components such as glutathione. Synthetic modifications may also be incorporated to promote binding to membranes, liposomes or polymers. These include addition of lipophilic groups such as fatty-acid amides (Example 8) or esters, phospholipids, ethers or polyethers or alkyl chains of about 12 to approximately 24 carbon atoms. Commonly the modification is a polymer that is water miscible or immiscible. Examples of suitable polymers include polysaccharides such as dextrans (Example 11), peptides and proteins (Example 12), and polystyrene.

Detection of Ions

The indicator is combined with a sample in a way that will facilitate detection of the ion concentration in the sample. The sample is generally a fluid or liquid suspension that is known or suspected to contain the target ion. Representative samples include intracellular fluids such as in blood cells, cultured cells, muscle tissue, neurons and the like (Example 24); extracellular fluids in areas immediately outside of cells; in vesicles; in vascular tissue of plants and animals; in biological fluids such as blood, saliva, and urine; in biological fermentation media; in environmental samples such as water, soil, waste water and seawater; and in chemical reactors.

The indicator is generally combined by dissolving the indicator in solution at a concentration that is optimal for detection of the fluorescence. Initially, the suitability of a material as an indicator of ion concentration is commonly tested by mixing a constant amount of the indicating reagent with a measured amount of the target ion whose concentration is to be estimated. The optical response of the indicating reagent is determined by absorbance changes or, more commonly by fluorescence changes. If absorbance measurements are used, then it is usually optimal to adjust the optical density of the indicator over the range of analyte concentration to a value of approximately 0.02 to 2.5 (most preferably 0.1 to 1). For fluorescence measurements the concentration of the indicator will depend mostly on the sensitivity of the equipment used for its detection.

Measurements are typically done at indicator concentrations of $10^{-9}$ to $10^{-4}$M. The most useful range of analyte concentration is about one log unit above and below the dissociation constant of the ion-indicator complex. This dissociation constant is obtained by titration of the indicator with known concentrations of the target ion usually over the range of from zero concentration to approximately 0.2 to 1 molar of the target ion (Examples 19–22). The dissociation constant may be affected by the presence of other ions, particularly ions that have similar ionic radii and charge. It may also be affected by other conditions such as ionic strength, pH, temperature, viscosity, presence of organic solvents and incorporation of the sensor in a membrane or polymeric matrix or binding of the sensor to a protein or other biological molecule. Any or all of these effects need to be tested to calibrate an indicator. Preferred are indicators whose absorption (or excitation) spectrum or fluorescence emission spectrum shifts on ion binding. Also preferred are indicators that have a high rejection of non-target ions. This ability to reject a non-target ion can be tested by a comparable titration of the indicator with that ion.

The optical response of the indicator to the ion can be detected by various means that include measuring absorbance changes with an instrument or visually or by a fluorescence sensing device. Several examples of fluorescence sensing devices are known such as fluorometers, fluorescence microscopes, laser scanners, and flow cytometers as well as by cameras and other imaging equipment. These measurements may be made remotely by incorporation of the fluorescent ion sensor as part of a fiber optic.

Modifications that are designed to enhance permeability of the indicator through the membrane of living cells such as acetoxymethyl esters and acetates may require the indicator to be predissolved in an organic solvent such as dimethylsulfoxide (DMSO) before adding to a cell suspension, where the indicators then readily enter the cells. Intracellular enzymes cleave the esters to the more polar acids and phenols that are then well retained inside the cells.

The examples below are given so as to illustrate the practice of this invention. They are not intended to limit or define the entire scope of the invention.

Example 1: Synthesis of a bis-(4-nitro-2,5-dimethoxyphenyl)-diazatrioxa crown ether (Compound II) Compound 1 (bis-(2,5-dimethoxyphenyl)-diazatrioxa crown ether) (500 mg, 1.02 moles) (as described in U.S. Pat. No. 5,134,232 to Tsien, et al.) is dissolved in 2.0 mL glacial acetic acid and 135 mg (2.15 moles) 70% $HNO_3$ is added in 25 µL aliquots over two minutes. The reaction forms a nonpolar yellow product with $R_f$=0.5 in ethyl acetate. The reaction is diluted with 50 mL $CHCl_3$ and washed four times with 100 mL deionized water. The brown organic layer is evaporated under reduced pressure to give a thick oil. This is dissolved in 5 mL $CHCl_3$ and purified on 100 mL silica gel (0.04–0.06 mm) that is eluted with 10% ethyl acetate in $CHCl_3$. The pure column fractions are evaporated to a clear yellow oil, which crystallizes on trituration with methanol to give 190 mg (Compound II). The NMR in $CDCl_3$ shows 3.6–3.8 ppm 20H (m); 3.85 ppm 6H (s); 3.95 ppm 6H (s); 7.55 ppm 4H (s).

Example 2: Synthesis of a bis-(4-amino-2,5-dimethoxyphenyl)-diazatrioxa crown ether (Compound III). Compound II (150 mg) is dissolved in 5 mL N,N-dimethylformamide (DMF) and the solution is hydrogenated at 25 psi for two hours. A TLC of the colorless reaction shows complete conversion of II to a polar product that reacts with ninhydrin on TLC to give a blue-colored product. The reaction is filtered to remove the catalyst and the filtrate is diluted to 50 mL with ethyl acetate. The colorless solution is washed three times with 100 mL deionized water and then evaporated under reduced pressure to give 60 mg of a light yellow oil (Compound III) that is >95% pure on TLC in 3% acetic acid/10% methanol/87% chloroform.

Example 3: Conjugation of a bis-(4-amino-2,5-dimethoxyphenyl)-diazatrioxa crown ether to two identical green fluorescent dyes (2',7'-dichlorofluorescein) by carboxamide linkages (Compound VI). 5-carboxy-2',7'-dichlorofluorescein diacetate (2.0 g, Molecular Probes, Inc., Eugene, Oreg.) is dissolved in 20 mL $CH_2Cl_2$ to give a clear solution. The stirred solution is cooled to 0° C. and 0.43 g (4.36 mmoles) triethylamine is added. After five minutes, 0.64 g (4.67 mmoles) of isobutyl chloroformate is added and the reaction is stirred at 20° C. for three hours, at which time TLC analysis shows that the starting acid has been completely converted to the mixed anhydride. The solvent is evaporated and the residue is redissolved in ethyl acetate. The colorless triethylamine hydrochloride is filtered and the clear filtrate is evaporated at 15° C. to give a colorless oil that dries to a foam under high vacuum. The yield is 2.2 g (3.5 mmoles; 90% yield) (Compound IV). NMR in $CDCl_3$ shows 1.55 ppm 6H (s); 2.35 ppm 6H (s); 3.95 ppm 1H (s); 4.4 ppm 2H (q); 6.85 ppm 2H (s); 7.2 ppm 2H (s); 7.85 ppm 1H (s); 8.15 ppm 1H (d); 8.35 ppm (m).

Compound III (0.030 g) is dissolved in 1.2 mL $CHCl_3$ to give a clear solution. 5-carboxy-2',7'-dichlorofluorescein diacetate (0.075 gm) isobutyl mixed anhydride (Compound IV) is added as a clear solution in 1.0 mL $CHCl_3$ and the resulting yellow solution is stirred at room temperature for 14 hours. A TLC in 1% acetic acid/10% methanol/89% $CHCl_3$ shows a new product formed with an $R_f$ of 0.45 that becomes fluorescent on exposure to ammonium hydroxide fumes. This product is isolated by purification on 50 mL silica gel (0.04–0.06 mm) eluted in 5% methanol in $CHCl_3$ to remove the excess reactive fluorescein. The product is eluted with 1% acetic acid/10% methanol/89% $CHCl_3$ to give 14 mg of a clear oil (Compound V). NMR in $CDCl_3$ shows 2.35 ppm 12H (s); 3.6–4.3 32 H (m); 6.85 ppm 4H (d); 7.2 ppm 4H (d); 7.4 ppm 2H (d); 83 ppm 2H (m); 8.5 ppm 3 H (s).

4.0 mg of the bis-fluorescein conjugate (Compound V) is dissolved in 25 µL dioxane and 25 µL methanol to give a clear solution. 3 µL ammonium hydroxide (30% aqueous) is added and the reaction turns red immediately. A TLC after 20 minutes shows complete conversion of the tetraacetate to a polar product that has weak green fluorescence. This is purified by diluting the reaction mixture with 300 µL of deionized water and loading on a reverse-phase column of 7 mL lipophilic SEPHADEX LH-20. The product is eluted with deionized water as a red band. The extinction coefficient of this product is 160,000 $cm^{-1}M^{-1}$ at 510 nm in methanol, which confirms the presence of two dichlorofluorescein moieties (Compound VI). The absorption spectra measured in zero and in saturating $Na^+$ (135 mM) give extinction coefficients of 98,038 $cm^{-1}M^{-1}$ at 504 nm and 104,539 $cm^{-1}M^{-1}$ at 508.4 nm respectively. The shape of the absorbance curve becomes sharper on ion binding, which suggests that there is some interaction between fluorophores at low ion concentrations.

Example 4: Conjugation of an N,N-bis-(aminophenyl)-diazatrioxa crown ether to two identical orange fluorescent dyes (tetramethylrhodamine) by thiourea linkages (Compound VIII). Compound III (30 mg) is dissolved in 1.0 mL DMF and 15 mg tetramethylrhodamine-5-isothiocyanate (Molecular Probes, Inc. Eugene, Oreg.) (Compound VII) is added as a purple solution in 1.3 mL DMF. The dark solution is stirred at room temperature for 14 hours. A TLC in 5% acetic acid/15% methanol/85% $CHCl_3$ shows a new deep purple product formed with an $R_f$ between that of the diamino crown ether and the reactive rhodamine.

The fluorescence is very dim in comparison to the starting rhodamine. The DMF is removed under reduced pressure and the resulting purple gum is redissolved in $CHCl_3$ and purified on 50 mL of silica gel eluted in 3% acetic acid/15% methanol/82% $CHCl_3$. Pure fractions yield 20 mg of a purple oil (Compound VIII).

Example 5: Synthesis of a diaryldiazatrioxa crown ether with one reactive amine function (Compound IX). Compound III (50 mg) is dissolved in 10 mL DMF and then reduced under 25 psi hydrogen pressure in the presence of 10 mg 10% palladium on charcoal for 30 minutes. A TLC in ethyl acetate shows a mixture of II, III and an intermediate $R_f$ product that is both yellow and light sensitive. This compound reacts with ninhydrin to give a brown-blue product. The catalyst is removed by filtration and the yellow filtrate is diluted to 50 mL with ethyl acetate and washed four times with 100 mL deionized water. The organic layer is evaporated under reduced pressure and the resulting brown oil is purified on 75 mL silica gel. The remaining II is removed by eluting with ethyl acetate and the product is eluted with 5% methanol in ethyl acetate. Pure column fractions yield 19 mg of a tan oil (Compound IX).

Example 6: Synthesis of a conjugate of bis-(aminophenyl)-diazatrioxa crown ether with one orange fluorescent dye (tetramethylrhodamine) linked by a thiourea linkage and one reactive amine group (Compound X). Compound III (50 mg) is dissolved in 2 mL DMF and one equivalent of tetramethylrhodamine-5-isothiocyanate (Compound VII) is added dropwise as a solution in one mL DMF. The TLC after stirring for one hour shows no isothiocyanate remains and one major purple product formed that is more polar and much less fluorescent than the reactive rhodamine. Reaction with ninhydrin gives a slight darkening of the product on TLC plates. This product is isolated by column chromatography and the pure fractions are combined and evaporated to a purple semi-solid (Compound X).

Example 7: Synthesis of a conjugate of bis-(aminophenyl)-diazatrioxa crown ether with one orange fluorescent dye (tetramethylrhodamine) linked by a thiourea linkage and one reactive isothiocyanate group (Compound XI). Compound X (10 mg) is dissolved in 1 mL $CHCl_3$ and 5 equivalents (3 μL) of thiophosgene are added in one portion. The solution becomes a darker purple and after stirring for one hour a purple precipitate forms. TLC analysis of the reaction shows conversion of the amine to a higher $R_f$, nonfluorescent purple product. The reaction mixture is centrifuged and the pellet is washed three times with hexanes and dried under vacuum for two days. The purple solid is over 90% pure to TLC in 1% acetic acid/10% methanol/89% $CHCl_3$ with a mass of 11 mg (Compound XI).

Example 8: Synthesis of a conjugate of bis-(aminophenyl)-diazatrioxa crown ether with one orange fluorescent dye (tetramethylrhodamine) linked by a thiourea linkage and one single chain lipid (Compound XII). Compound XI (10 mg) is dissolved in 1 mL DMF and excess octadecylamine (10 mg) is added as a solid. TLC after stirring for three hours shows no reactive crown ether remains and the formation of a single, more polar, orange fluorescent product. This is isolated by column chromatography in 20% methanol/$CHCl_3$, the major purple band collected as one fraction and evaporated under reduced pressure to yield a purple oil (Compound XII). The NMR in $CDCl_3$ confirms the presence of the crown ether, a single rhodamine and a single C18 carbon chain.

Example 9: Synthesis of a conjugate of bis-(aminophenyl)-diazatrioxa crown ether with one green fluorescent dye (2', 7'-dichlorofluorescein) and one reactive amine group (Compound XIII. Compound III (50 mg) is dissolved in 3 mL $CHCl_3$ to give a clear solution. 1.0 equivalents of 5-carboxy-2',7'-dichlorofluorescein diacetate isobutyl mixed anhydride (Compound IV) is added as a clear solution in 1.0 mL $CHCl_3$ and the resulting yellow solution is stirred at room temperature for six hours. TLC in 1% acetic acid/10% methanol/89% $CHCl_3$ shows complete conversion of II to a higher $R_f$ product that becomes red on exposure to ammonia vapor. Reaction with ninhydrin gives a ruddy brown product on TLC. The reaction mixture is diluted to 5 mL with $CHCl_3$ and loaded directly onto a silica gel column packed and eluted in 10% methanol in $CHCl_3$. The product is eluted with 1% acetic acid/10% methanol/89% $CHCl_3$ to give 35 mg of the mono-fluorescein conjugate as a colorless oil.

The acetate protecting groups are removed by dissolving the above oil in 2 mL dioxane/methanol (1:1) and adding 15 μL of ammonium hydroxide (30% aqueous). A TLC of the red solution shows conversion to a lower $R_f$, red product with dim green fluorescence. The solvents are removed under vacuum to yield 28 mg of the tetraammonium salt (Compound XIII) as an opaque red oil.

Example 10: Synthesis of a conjugate of bis-(aminophenyl)-diazatrioxa crown ether with one green fluorescent dye (2',7'-dichlorofluorescein) and one reactive isothiocyanate group (Compound XIV). Compound XIII (10 mg) is suspended in 2 mL dry acetone and stirred at room temperature for 30 minutes. 3 μL of thiophosgene is added in one portion; within five minutes all the solid dissolves and the color of the solution changes from red to light brown. TLC in 1% acetic acid/10% methanol/$CHCl_3$ shows complete conversion of the amine to a higher $R_f$ brown/red product that does not react with ninhydrin. The acetone is evaporated under reduced pressure and the resulting brown solid is dried for 12 hours under vacuum to remove traces of thiophosgene to yield 10 mg of the reactive fluorescent crown ether (Compound XIV).

Example 11: Synthesis of a conjugate of bis-(aminophenyl)-diazatrioxa crown ether with one green fluorescent dye (2',7'-dichlorofluorescein) and one water soluble polymer (Compound XV). 100 mg of a 70,000 MW aminodextran (average of 30 amines/dextran) is dissolved in 2 mL DMSO by stirring at room temperature for 30 minutes. Compound XIV (10 mg) is dissolved in 0.5 mL DMSO and the light yellow solution added dropwise to the stirring aminodextran solution over three minutes. On addition of the reactive indicator the solution turns bright red with strong fluorescence. The reaction is stirred at room temperature until a TLC shows that over 90% of compound XIV is consumed. The reaction is added to 25 mL of stirring acetone and the orange flocculent suspension is collected by filtration using a fritted glass funnel. The solid is dissolved in approximately 10 mL deionized water and 0.2 mL acetic anhydride is added to the solution while the pit is kept above 8 by addition of 40% tetramethylammonium hydroxide. The pH is adjusted to 8.5 and the red solution is transferred to a presoaked dialysis tubing (MW cutoff of 12–14,000 Daltons). The dextran conjugate is dialyzed versus 1 L deionized water (2×3 hours) and 1 L pH 7.5 tetramethylammonium hydroxide (2×12 hours) to remove any unreacted dye. The orange solution that remains in the dialysis tubing is transferred to a flask, frozen and lyophilized to give 95 mg light red/orange solid (Compound XV). This conjugate responds to changes in sodium concentration with an increase in fluorescence emission intensity essentially identical to compound VI and based on an extinction coefficient of 75,000 cm$^{-1}$M$^{-1}$ is labeled with 5.2 dyes/dextran (see Example 22).

Example 12: Preparation of a conjugate of a diaryldiazatrioxa crown ether with one green fluorescent (2',7'-dichlorofluorescein) dye and a biopolymer linked by a thiourea linkage (Compound XVI). Compound XIV (5 mg) is added to a solution of 25 mg keyhole limpet hemocyanin (KLH, Calbiochem, La Jolla, Calif.) in 1.5 mL sodium bicarbonate buffer, pH 9. The reaction is stirred at room temperature for ~14 hours. It is then diluted with 2.0 mL deionized water and applied to a SEPHADEX G-25 gel filtration column eluted with pH 7.5 phosphate buffered saline to remove any unreacted dye. The fluorescent KLH band is collected and lyophilized to give a light orange powder (Compound XVI).

Example 13: Synthesis of a diaryldiaza crown ether that contains one green fluorescent dye (2',7'-dichlorofluorescein) linked by a carboxamide linkage and a thiol reactive iodoacetamide (Compound XVII). Compound VI (25 mg) in 1 mL water is treated by dropwise addition of 25 mg iodoacetic anhydride dissolved in 0.5 mL acetonitrile. The crude iodoacetamide (Compound XVII) is isolated by precipitation with acetone and washed with ether. The product is stored protected from light.

Example 14: Preparation of a conjugate of a diaryldiaza crown ether that contains one green fluorescent dye (2',7'-dichlorofluorescein) and is linked to a liposome through a thioether linkage. (Compound XVIII). Dioleoyl phosphocholine (DOPC) liposomes containing thiolated phosphoethanolamine (derived by reduction of N-((2-pyridyldithio)propionyl)-1,2-dihexadecanoyl-sn-glycero-3-phosphoethanolamine, triethylammonium salt (Molecular Probes, Inc., Eugene, Oreg.) with dithiothreitol according to the method described for this compound by Heath in Methods in Enzymology 149, 111 (1987)) is treated with compound XVII at pH 7.6 for 2 hours. The ion-selective fluorescent liposome (Compound XVIII) is isolated by purification on a SEPHADEX G-25 column.

Example 15: Synthesis of a bis-(4-nitrophenyl)-diazatetraoxa crown ether (Compound XIX). KRYPTOFIX 22 (0.5 gm, Aldrich Chemical Co.) is dissolved in 5 mL dry pyridine and six equivalents of p-fluoronitrobenzene are added. The dark reaction is refluxed for 13 hours until a TLC in ethyl acetate/CHCl$_3$ 1:1 shows conversion of most of the starting crown ether to a yellow product with an R$_f$ of 0.6. The pyridine is evaporated under reduced pressure and the brown oil is purified on 150 mL silica gel eluted in CHCl$_3$ to remove the excess p-fluoronitrobenzene and then with 20% ethyl acetate/80% CHCl$_3$ to elute the product as a yellow band. The pure fractions are evaporated to give a clear yellow oil that crystallizes on trituration with methanol to yield 0.23 gm yellow solid (Compound XIX).

Example 16: Synthesis of a bis-(4-aminophenyl)-diazatetraoxa crown ether (Compound XX). Compound XIX is reduced to the diamine by hydrogenation in DMF at 30 psi in the presence of 10% palladium on charcoal. The colorless reaction is filtered and the DMF is removed under reduced pressure to yield Compound XX as a grey oil.

Example 17: Conjugation of a bis-(4-aminophenyl)-diazatetraoxa crown ether to two identical green fluorescent dyes (2',7'-dichlorofluorescein) by carboxamide linkages (Compound XXII). Compound XX (0.1 gm) from Example 16 is dissolved in 1 mL DMF to give a light grey solution. Three molar equivalents of Compound IV are added dropwise to the stirring diamine solution over five minutes and the resulting light yellow solution is stirred for five hours until TLC in 3% acetic acid/15% methanol/82% CHCl$_3$ shows no amine remains. A high R$_f$ (0.8) UV quenching product is formed that turns red on exposure to ammonia vapor and reacts with ninhydrin to give a brown product. The reaction is diluted with 20 mL ethyl acetate and is washed three times with deionized water. The organic layer is evaporated and the yellow oil is purified on 75 mL silica gel eluted with 10% methanol/CHCl$_3$. The pure product fractions are combined and evaporated to a light yellow oil (Compound XXI), which is pure to TLC in 10% methanol/90% CHCl$_3$. This oil is dissolved in 1:1 methanol:dioxane and five molar equivalents of ammonium hydroxide are added to immediately give a red solution. After stirring for two hours, TLC in 10% methanol/90% CHCl$_3$ shows all of Compound XXI is converted to a polar red product with very dim green fluorescence. The reaction is evaporated and the red oil is dissolved in 2 mL deionized water and purified by reverse phase column chromatography. The red band is collected as one fraction, which is frozen and lyophilized to give a flocculent red solid (Compound XXII).

Example 18: Conjugation of a bis-(4-aminophenyl)-diazatrioxa crown ether to two identical red fluorescent dyes (Sulforhodamine 101) by sulfonamide linkages (Compound XXIII). Compound XX (100 mg) is dissolved in 1 mL dry DMF to give a grey solution. TEXAS RED™ sulfonyl chloride (350 mg, Molecular Probes, Inc; Eugene, Oreg.) is added in one portion with stirring under N$_2$. The reaction is stirred for 30 minutes until TLC in 3% acetic acid/15% methanol/82% CHCl$_3$ shows all the diamine is converted to a lower R$_f$ product. The DMF is removed under reduced pressure to yield a red oil that is dissolved in 5 mL deionized water and stirred for twenty minutes to hydrolyse any remaining sulfonyl chloride. The dark purple solution is purified by reverse phase column chromatography (SEPHADEX LH-20) eluting with pH 7.5 ammonium hydroxide. The product elutes as a deep purple band, which is collected as one fraction, frozen and lyophilized to give a red/purple flocculent solid (Compound XXIII).

Figure 6:
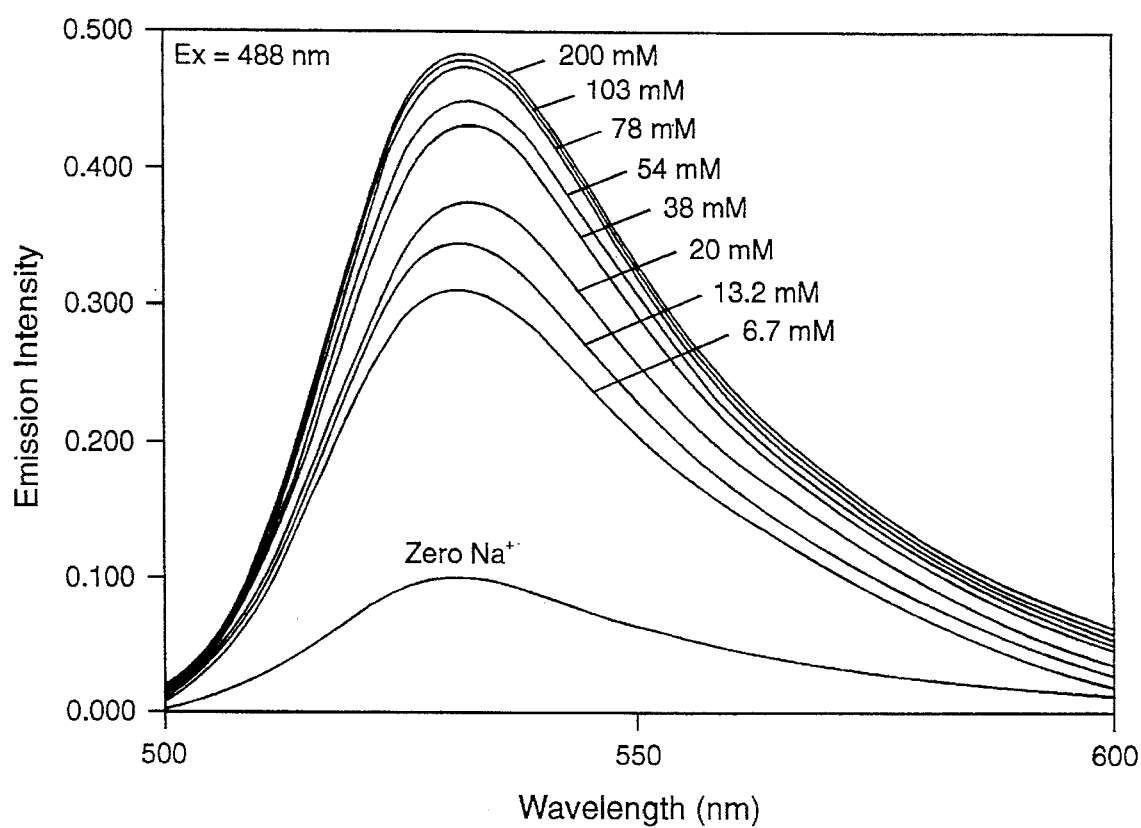
FIG. 6: $Na^+$ binding affinity of a fluorescent diaryldiazatrioxa crown ether with two identical green fluorescent dyes (2',7'-dichlorofluorescein) attached by carboxamide linkages.

Example 19: Na$^+$ binding affinity of a fluorescent diaryldiaza crown ether with two identical green fluorescent dyes (2',7'-dichlorofluorescein) attached by carboxamide linkages. The binding affinity of Compound VI for Na$^+$ is determined by dissolving a sample of the purified ammonium salt from Example 3 in 3 mL of each of two solutions: solution 1 ("high Na$^+$") consists of 200 mM NaCl and 10 mM MOPS buffer at pH 7.05; solution 2 ("zero Na$^+$") of 10 mM MOPS buffer at pH 7.05 in deionized water. The curves as shown in FIG. 6 are generated by cross dilution between the two solutions to arrive at intermediate concentrations of Na$^+$. For example, the emission of the dye in solution 2 is scanned from 500 nm to 650 nm and then 1/100 of the sample is removed and replaced with 1/100 of solution 1 to arrive at a Na$^+$ concentration of 2 mM. This is repeated to cover the entire range from zero to 200 mM Na$^+$ and the resulting emission intensities are plotted versus the ion concentrations. A least-squares fit used to arrive at the concentration where the indicator is maximally sensitive to changes in Na$^+$ concentration. This is the dissociation constant for Na$^+$ and is expressed as a concentration. For Compound III, the K$_d$ for Na$^+$ is determined to be 8 mM.

Figure 7:
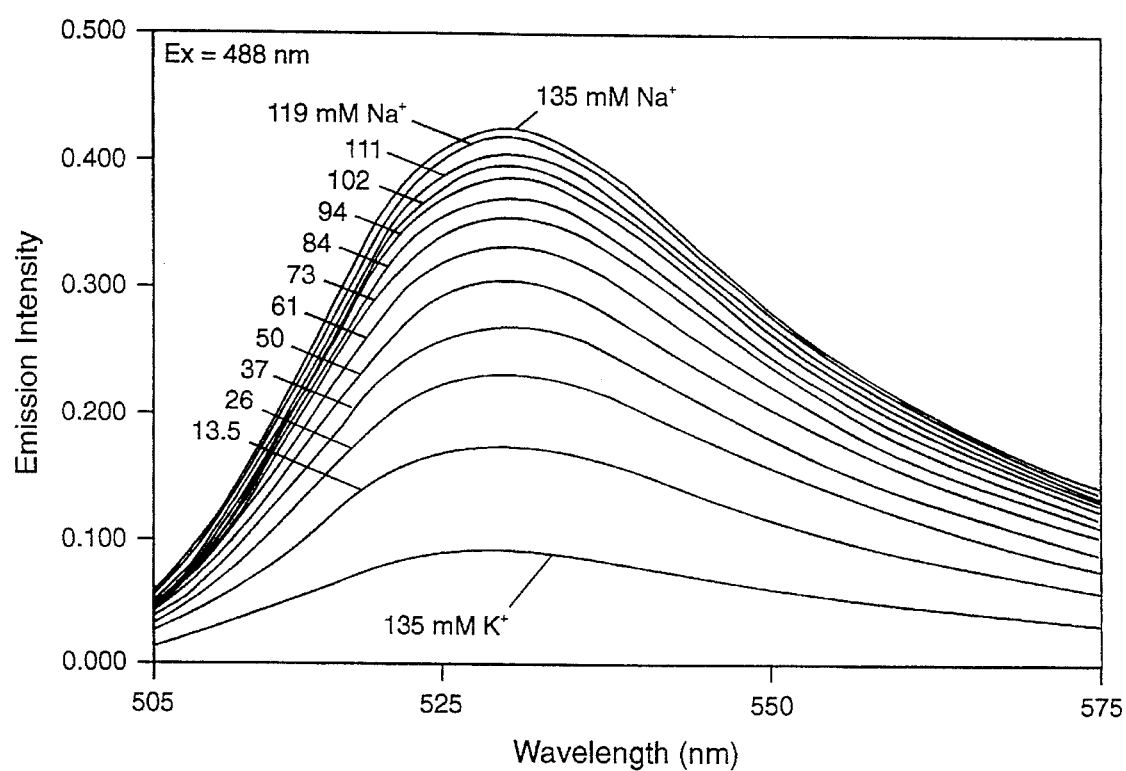
FIG. 7: $Na^+$ binding affinity in the presence of $K^+$ for a fluorescent diaryldiazatrioxa crown ether with two identical green fluorescent dyes (2',7'-dichlorofluorescein) attached by carboxamide linkages.

Example 20: Na+ binding affinity in the presence of K+ for a fluorescent diaryldiaza crown ether with two identical green fluorescent dyes (2',7'-dichlorofluorescein) attached by carboxamide linkages. Because the crown ethers used as the ion binding site of these indicators can bind both Na+ and K+, the $K_d$ for Na+ is determined in the presence of K+ while keeping the ionic strength constantly 135 mM. The binding affinity of Compound VI for Na+ in the presence of K+ is determined by dissolving a sample of the purified ammonium salt from Example 3 in 3 mL of each of two solutions: solution 1 ("high Na+") consists of 135 mM NaCl and 10 mM MOPS buffer at pH 7.05; solution 2 ("high K+") consists of 135 mM KCl and 10 mM MOPS buffer at pH 7.05 in deionized water. Fluorescence of the Na+ solution is approximately 8 times brighter than the sample containing K+, as shown in FIG. 7. The intermediate curves are generated by cross dilution between the two solutions to arrive at intermediate concentrations of Na+ and K+ where the total of both ions remains 135 mM. Calculating the dissociation constant for Na+ as described in Example 18 gives a maximum sensitivity to Na+ at 30 mM.

Figure 8:
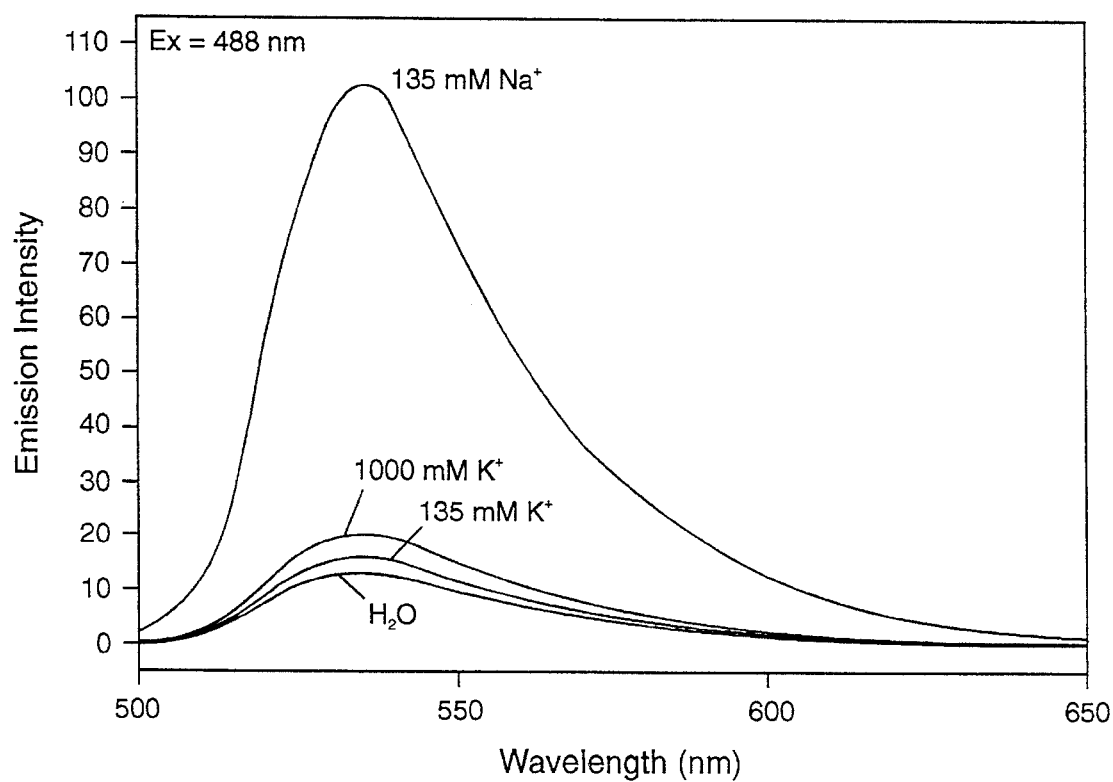
FIG. 8: Relative intensities of saturating $Na^+$ and $K^+$ for a fluorescent diaryldiazatrioxa crown ether with two identical green fluorescent dyes (2',7'-dichlorofluorescein) attached by carboxamide linkages.

Example 21: Relative intensities of Na+ and K+ for a fluorescent diaryldiaza crown ether with two identical green fluorescent dyes (2',7'-dichlorofluorescein) attached by carboxamide linkages. A comparison of the absolute intensity changes for compound III between zero and saturating Na+ (135 mM) is compared with the intensity between zero, 135 mM and 1,000 mM K+. FIG. 8 shows that even at extremely high K+ concentrations, the emission intensity increases less than 20%. This shows that Compound VI discriminates between these two ions very effectively and that large changes in fluorescence can result from sodium binding only.

Example 22: Ion binding affinity of a water soluble diaryldiaza crown ether conjugate of a polymer (dextran) with one green fluorescent (2',7'-dichlorofluorescein) dye. The affinity of a fluorescent crown ether conjugate is determined by dissolving 5 mg of the labeled dextran (Compound XV) in 1 mL deionized water and diluting 50 µL into 3 mL each of high Na+ and high K+ buffer, as in Example 19. The emission spectra of the dye solutions are scanned between dilution while exciting at 488 nm. The emission response is similar to that of the free indicator, Compound VI.

Example 23: Determining the degree of labeling for a water soluble diaryldiaza crown ether conjugate with one green fluorescent (2',7'-dichlorofluorescein) dye. A 50 µL aliquot of the stock solution from Example 21 is diluted into 3 mL of 135 mM KCl, 10 mM MOPS buffer at pH 7.05 the absorption spectra of the two solutions are scanned. The degree of labeling is then calculated by a comparison of the extinction coefficient of the labeled dye at 510 nm with that of free 5-carboxy-2',7'-dichlorofluorescein. In this way, the number of dyes covalently bound to an average molecular weight dextran can be determined. Based on an extinction coefficient of 79,000 cm$^{-1}$M$^{-1}$ the degree of substitution of the dextran conjugate synthesized in Example 11 (Compound XV) is approximately 5.2 dyes/70,000 MW dextran.

Example 24: Intracellular response of a cell-permanent, fluorescent indicator for Na+ (Compound V). Compound V (1.0 mg) is dissolved in 1 mL dry DMSO and diluted into phosphate-buffered saline to give a final dye concentration of 2 µM. 3T3 fibroblasts are incubated in the dye solution for 30 minutes and then washed with PBS buffer. Fluorescence microscopy of the cells using a 480–500 nm excitation source shows that the cells have a dim green fluorescence. Addition of 5 µM gramicidin D (an ionophore that equilibrates extracellular and intracellular Na+ levels) to the extracellular solution causes a visible increase in the fluorescence emission intensity of the intracellular dye.

It is to be understood that, while the foregoing invention has been described in detail by way of illustration and example, numerous modifications, substitutions, and alterations are possible without departing from the spirit and scope of the invention as described in the following claims.

What is claimed is:
1. A fluorescent ion-selective compound having the formula:

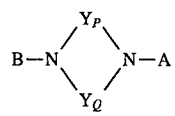

where $Y_p$ is —(CH$_2$CH$_2$—O)$_j$—CH$_2$CH$_2$— and $Y_Q$ is —(CH$_2$CH$_2$—O)$_k$—CH$_2$CH$_2$—; j and k are independently 1 or 2;
where A is a substituted aryl of the formula:

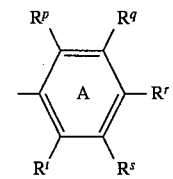

where at least one of R$^p$, R$^q$, R$^r$, R$^s$ and R$^t$ is a fluorophore according to the formula:

(R$^a$)$_n$(R$^b$)$_{n'}$-FLUOR, wherein n=0 or 1; n'=0 or 1; R$^a$ is —OCH$_2$R$^3$—, —OR$^{3'}$—, —SR$^3$—, —SR$^{3'}$—, —NH(C=O)CH$_2$R$^3$—, —NH(C=O)R$^{3'}$—, —(C=O)NHCH$_2$R$^3$—, —(C=O)NHR$^{3'}$—, —NHSO$_2$R$^3$—, —NHSO$_2$R$^{3'}$—, —NH(C=O)NHCH$_2$R$^3$—, —NH(C=O)NHR$^{3'}$—, —NH(C=S)NHCH$_2$R$^3$—, or —NH(C=S)NHR$^{3'}$—, where R$^3$ is (CH$_2$)$_m$ and m=1–6, and R$^{3'}$ is phenylene (—C$_6$H$_4$), carboxyphenylene (—C$_6$H$_3$COOH—) or sulfophenylene (—C$_6$H$_3$SO$_3$H—) or the pharmaceutically acceptable salt or ester thereof; R$^b$ is —NH—, —NH(C=O)—, —NH(C=S)—, —S—, —O—, —(C=O)—; or —CH$_2$— or —(C=O)CH$_2$—; and
-FLUOR is a substituted xanthylium fluorophore;
where the remaining A substituents R$^p$, R$^q$, R$^r$, R$^s$, and R$^t$, which may be the same or different, are independently H, CH$_3$, NO$_2$, CF$_3$, F, Cl, Br, I, —OR$^5$, —(C=O)OR$^5$, or —OCH$_2$(C=O)OR$^5$, where R$^5$ is an alkyl group with about 1–6 carbons, a benzyl (C$_6$H$_5$CH$_2$—), an alpha-acyloxyalkyl or a pharmaceutically acceptable esterifying group, or a pharmaceutically acceptable salt;
where B is a substituted aryl of the formula:

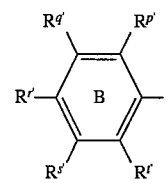

where at least one of R$^{p'}$, R$^{q'}$, R$^{r'}$, R$^{s'}$ and R$^{t'}$ contains a reactive terminus R$^x$;

or one of $R^{p'}$, $R^{q'}$, $R^{r'}$, $R^{s'}$ and $R^{t'}$ has the formula:

$(R^{a'})_n(R^{b'})_{n'}$—X wherein n=0 or 1; n'=0 or 1; $R^{a'}$ is —OCH$_2$R$^3$—, —OR$^{3'}$—, —SR$^3$—, —SR$^{3'}$—, —NH(C=O)CH$_2$R$^3$—, —NH(C=O)R$^{3'}$—, —(C=O)NHCH$_2$R$^3$—, —(C=O)NHR$^{3'}$, —NHSO$_2$R$^3$—, —NHSO$_2$R$^{3'}$—, —NH(C=O)NHCH$_2$R$^3$—, —NH(C=O)NHR$^{3'}$—, —NH(C=S)NHCH$_2$R$^3$—, or —NH(C=S)NHR$^{3'}$—, where R$^3$ is (CH$_2$)$_m$ and m=1–6, and R$^{3'}$ is phenylene (—C$_6$H$_4$—), carboxyphenylene (—C$_6$H$_3$COOH—) or sulfophenylene (—C$_6$H$_3$SO$_3$H—) or the pharmaceutically acceptable salt or ester thereof; R$^{b'}$ is —NH—, —NH(C=O)—, —NH(C=S), —S—, —O—, —(C=O)—; or —CH$_2$— or —(C=O)CH$_2$—; and -X is a polymolecular assembly -POLY;

or -X is a lipophilic moiety (-LIPID); and where the remaining B substituents $R^{p'}$, $R^{q'}$, $R^{r'}$, $R^{s'}$ or $R^{t'}$, which may be the same or different, are independently H, CH$_3$, NO$_2$, CF$_3$, F, Cl, Br, I, —OR$^5$, —(C=O)OR$^5$, or —OCH$_2$(C=O)OR$^5$, where R$^5$ is an alkyl group with about 1–6 carbons, a benzyl (C$_6$H$_5$CH$_2$—), an alpha-acyloxyalkyl or a pharmaceutically acceptable esterifying group, or a pharmaceutically acceptable salt.

2. A compound as in claim 1 where $R^p$, $R^q$, $R^r$, $R^s$ or $R^t$ is $(R^a)_n(R^b)_{n'}$-FLUOR, where FLUOR is a pyronine, xanthene, fluorescein, rhodamine, rosamine, rhodol, benzofluorescein, dibenzofluorescein, seminaphthofluorescein, or naphthofluorescein, or a pharmaceutically acceptable salt or ester thereof.

3. A compound as in claim 1 where $R^r$ is $(R^a)_n(R^b)_{n'}$-FLUOR.

4. A compound as in claim 1 where j=2 and k=1.

5. A compound as in claim 1 where j=2 and k=2.

6. A compound as in claim 1 where the substituted phenyl B contains a reactive terminus R$^x$ that is an amine, an aniline, an alcohol, a phenol, a haloacetamide, a maleimide, an alkyl halide, an alkyl sulfonate, a thiol, a carboxylic acid, an anhydride, an activated ester, an acyl halide, an acyl azide, an isocyanate or an isothiocyanate.

7. A compound as in claim 1 where $R^{p'}$, $R^{q'}$, $R^{r'}$, $R^{s'}$ or $R^{t'}$ has the formula:

$(R^{a'})_n(R^{b'})_{n'}$—X.

8. A compound as in claim 7 where X is -POLY with a molecular weight between about 1,000 and about 10,000,000 Daltons.

9. A compound as in claim 7 where X is LIPID and is branched or unbranched and is an alkyl, fatty acid, phospholipid, glyceride, polyethylene, sterol, or polyoxyethylene containing greater than about 6 methylene groups and fewer than about 30 catenated nonhydrogen atoms.

10. A fluorescent ion-selective compound having the formula:

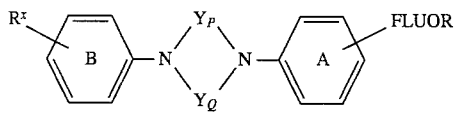

where $Y_p$ is —(CH$_2$CH$_2$—O)$_j$—CH$_2$CH$_2$— and $Y_Q$ is —(CH$_2$CH$_2$—O)$_k$—CH$_2$CH$_2$—; j and k are independently 1 or 2;

-FLUOR is a substituted xanthylium fluorophore that is linked to substituted aryl A by a first linkage that is a single covalent bond or is an ether, thioether, urea, thiourea, sulfonamide, carboxamide, or alkyl amine linkage;

-R$^x$ is a reactive terminus; and the remaining A and B substituents, which may be the same or different, are independently H, CH$_3$, NO$_2$, CF$_3$, F, Cl, Br, I, —OR$^5$, —(C=O)OR$^5$, or —OCH$_2$(C=O)OR$^5$, where R$^5$ is an alkyl group with about 1–6 carbons, a benzyl (C$_6$H$_5$CH$_2$—), an alpha-acyloxyalkyl or a pharmaceutically acceptable esterifying group, or a pharmaceutically acceptable salt.

11. A compound as in claim 10 where R$^x$ is a carboxylic acid, activated ester, acyl azide, anhydride, acid halide, acrylamide, alcohol, phenol, aldehyde, amine, aniline, aryl or alkyl azide, imido ester, sulfonate ester, haloacetamide, alkyl or aryl halide, sulfonyl halide, hydrazine, isocyanate, isothiocyanate, or a maleimide.

12. A compound as in claim 10 where j=2 and k=1 and -FLUOR is a pyronine, xanthene, fluorescein, rhodamine, rosamine, rhodol, benzofluorescein, dibenzofluorescein, seminaphthofluorescein, or naphthofluorescein, or a pharmaceutically acceptable salt or ester thereof.

13. A compound as in claim 12 where FLUOR is a fluorescein or a rhodamine, or a pharmaceutically acceptable salt or ester thereof, that is linked to the substituted aryl para to a crown nitrogen;

R$^x$ is an amine, an alcohol, a phenol, a haloacetamide, a maleimide, an alkyl halide, an alkyl sulfonate, a thiol, an aniline, a carboxylic acid, an anhydride, an activated ester, an isocyanate or an isothiocyanate that is para to a crown nitrogen; and the remaining A substituents and remaining B substituents are independently H or —OCH$_3$.

14. A compound as in claim 10 where j=2 and k=2 and -FLUOR is a pyronine, xanthene, fluorescein, rhodamine, rosamine, rhodol, benzofluorescein, dibenzofluorescein, seminaphthofluorescein, or naphthofluorescein, or a pharmaceutically acceptable salt or ester thereof.

15. A compound as in claim 14 where FLUOR is a fluorescein or a rhodamine, or a pharmaceutically acceptable salt or ester thereof, that is linked to the substituted aryl para to a crown nitrogen;

R$^x$ is an amine, an alcohol, a phenol, a haloacetamide, a maleimide, an alkyl halide, an alkyl sulfonate, a thiol, an aniline, a carboxylic acid, an anhydride, an activated ester, an isocyanate or an isothiocyanate that is para to a crown nitrogen; and the remaining A substituents and remaining B substituents are independently H or —OCH$_3$.

16. A fluorescent ion-selective compound having the formula:

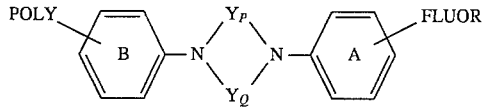

where $Y_p$ is —(CH$_2$CH$_2$—O)$_j$—CH$_2$CH$_2$— and $Y_Q$ is —(CH$_2$CH$_2$—O)$_k$—CH$_2$CH$_2$—; j and k are independently 1 or 2; and -FLUOR is a substituted xanthylium fluorophore that is linked to substituted aryl A by a first linkage that is a single covalent bond or is an ether, thioether, urea, thiourea, sulfonamide, carboxamide, or alkyl amine linkage;

-POLY is a polymolecular assembly that is linked to substituted aryl B by a second linkage that is a single covalent bond or is an ether, thioether, urea, thiourea, sulfonamide, carboxamide, or alkyl amine linkage; and the remaining A and B substituents, which may be the same or different, are independently H, CH$_3$, NO$_2$, CF$_3$, F, Cl, Br, I, —OR$^5$, —(C=O)OR$^5$, or —OCH$_2$(C=O)OR$^5$, where R$^5$ is an alkyl group with about 1–6 carbons, a benzyl ($C_6H_5CH_2$—), an alpha-acyloxyalkyl or a pharmaceutically acceptable esterifying group, or a pharmaceutically acceptable salt.

17. A compound as in claim 16 where -POLY is a natural or synthetic polysaccharide, polymeric resin, gel, glass, polyol, polypeptide, protein, oligonucleotide, nucleic acid polymer, liposome, or micelle.

18. A compound as in claim 16 where j=2 and k=1 and -FLUOR is a pyronine, xanthene, fluorescein, rhodamine, rosamine, rhodol, benzofluorescein, dibenzofluorescein, seminaphthofluorescein, or naphthofluorescein, or a pharmaceutically acceptable salt or ester thereof.

19. A compound as in claim 18 where -FLUOR is a fluorescein or a rhodamine, or a pharmaceutically acceptable salt or ester thereof, that is linked to the substituted aryl para to a crown nitrogen;
-POLY is a polysaccharide from about 1000 to about 500,000 Daltons that is linked para to a crown nitrogen; and
the remaining A substituents and remaining B substituents are independently H or —$OCH_3$.

20. A compound as in claim 18 where -FLUOR is a fluorescein or a rhodamine, or a pharmaceutically acceptable salt or ester thereof, that is linked to the substituted aryl para to a crown nitrogen;
-POLY is a water soluble polypeptide or protein from about 1000 to about 500,000 Daltons that is linked para to a crown nitrogen; and
the remaining A substituents and remaining B substituents are independently H or —$OCH_3$.

21. A compound as in claim 16 where j=2 and k=2 and -FLUOR is a pyronine, xanthene, fluorescein, rhodamine, rosamine, rhodol, benzofluorescein, dibenzofluorescein, seminaphthofluorescein, or naphthofluorescein, or a pharmaceutically acceptable salt or ester thereof.

22. A compound as in claim 21 where -FLUOR is a fluorescein or a rhodamine, or a pharmaceutically acceptable salt or ester thereof, that is linked to the substituted aryl para to a crown nitrogen;
-POLY is a polysaccharide from about 1000 to about 500,000 Daltons that is linked para to a crown nitrogen; and
the remaining A substituents and remaining B substituents are independently H or —$OCH_3$.

23. A compound as in claim 21 where -FLUOR is a fluorescein or a rhodamine, or a pharmaceutically acceptable salt or ester thereof, that is linked to the substituted aryl para to a crown nitrogen;
-POLY is a water soluble polypeptide or protein from about 1000 to about 500,000 Daltons that is linked para to a crown nitrogen; and
the remaining A substituents and remaining B substituents are independently H or —$OCH_3$.

24. A fluorescent ion-selective compound having the formula:

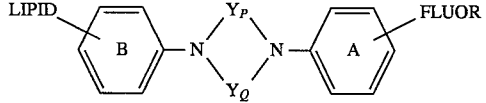

where $Y_P$ is —($CH_2CH_2$—O)$_j$—$CH_2CH_2$— and $Y_Q$ is —($CH_2CH_2$—O)$_k$—$CH_2CH_2$—; j and k are independently 1 or 2; and
-FLUOR is a substituted xanthylium fluorophore that is linked to substituted aryl A by a first linkage that is a single covalent bond or is an ether, thioether, urea, thiourea, sulfonamide, carboxamide, or alkyl amine linkage;
-LIPID is a lipophilic moiety that is linked to substituted aryl B by a second linkage that is a single covalent bond or is an ether, thioether, urea, thiourea, sulfonamide, carboxamide, or alkyl amine linkage; and
the remaining A and B substituents, which may be the same or different, are independently H, $CH_3$, $NO_2$, $CF_3$, F, Cl, Br, I, —$OR^5$, —(C=O)$OR^5$, or —$OCH_2$(C=O)$OR^5$, where $R^5$ is an alkyl group with about 1–6 carbons, a benzyl ($C_6H_5CH_2$—), an alpha-acyloxyalkyl or a pharmaceutically acceptable esterifying group, or a pharmaceutically acceptable salt.

25. A compound as in claim 24 where LIPID is branched or unbranched and is an alkyl, fatty acid, phospholipid, glyceride, polyethylene, sterol, or polyoxyethylene containing greater than about 6 methylene groups and fewer than about 30 catenated nonhydrogen atoms.

26. A compound as in claim 24 where j=2 and k=1 and -FLUOR is a pyronine, xanthene, fluorescein, rhodamine, rosamine, rhodol, benzofluorescein, dibenzofluorescein, seminaphthofluorescein, or naphthofluorescein, or a pharmaceutically acceptable salt or ester thereof.

27. A compound as in claim 26 where -FLUOR is a fluorescein or a rhodamine, or a pharmaceutically acceptable salt or ester thereof, that is linked to the substituted aryl para to a crown nitrogen;
-LIPID is a lipid chain containing between about 12 and about 20 linear carbon atoms that is linked para to a crown nitrogen; and
the remaining A substituents and remaining B substituents are independently H or —$OCH_3$.

28. A compound as in claim 24 where j=2 and k=2 and -FLUOR is a pyronine, xanthene, fluorescein, rhodamine, rosamine, rhodol, benzofluorescein, dibenzofluorescein, seminaphthofluorescein, or naphthofluorescein, or a pharmaceutically acceptable salt or ester thereof.

29. A compound as in claim 28 where -FLUOR is a fluorescein or a rhodamine, or a pharmaceutically acceptable salt or ester thereof, that is linked to the substituted aryl para to a crown nitrogen;
-LIPID is a lipid chain containing between about 12 and about 20 linear carbon atoms that is linked para to a crown nitrogen; and
the remaining A substituents and remaining B substituents are independently H or —$OCH_3$.

30. A fluorescent ion-selective compound comprising N,N'-diaryldiazacrown ether that is a DA15C5 or DA18C6 containing two aryl residues, wherein one aryl residue attached to the crown ether is covalently linked a first substituted xanthylium fluorophore and the other aryl residue attached to the crown ether contains a reactive terminus or is covalently linked to a polymolecular assembly or a lipophilic moiety.

* * * * *

UNITED STATES PATENT AND TRADEMARK OFFICE
CERTIFICATE OF CORRECTION

PATENT NO. : 5,516,864
DATED : May 14, 1996
INVENTOR(S) : Kuhn et al.

It is certified that error appears in the above-indentified patent and that said Letters Patent is hereby corrected as shown below:

At col 4, line 37, "—(=O)NHCH$_2$R$^3$—," should be -—(C=O)NHCH$_2$R$^3$—,--.

At col 4, line 40, "m+1-6," should be --m=1-6,--.

At col 5, line 43, "(C$_6$H$_5$CH$_2$—," should be --(C$_6$H$_5$CH$_2$—),--.

At col 6, line 22, "Where n'" should be --Where n and n'--.

At col 7, line 52, "($_{C6}$H$_3$COOH—)" should be --(—C$_6$H$_3$COOH—)--.

Signed and Sealed this

Thirtieth Day of July, 1996

BRUCE LEHMAN

*Attest:*

*Attesting Officer*     *Commissioner of Patents and Trademarks*